United States Patent
Sato et al.

(10) Patent No.: US 8,521,243 B2
(45) Date of Patent: Aug. 27, 2013

(54) BIOLOGICAL OPTICAL MEASUREMENT INSTRUMENT

(75) Inventors: Hiroki Sato, Shiki (JP); Akiko Obata, Kawagoe (JP); Atsushi Maki, Fuchu (JP); Kazutaka Ozaki, Kashiwa (JP); Takaomi Yasuhara, Moriya (JP); Ichiro Moda, Moriya (JP)

(73) Assignee: Hitachi, Ltd., Tokyo (JP)

( * ) Notice: Subject to any disclaimer, the term of this patent is extended or adjusted under 35 U.S.C. 154(b) by 1625 days.

(21) Appl. No.: 12/014,311

(22) Filed: Jan. 15, 2008

(65) Prior Publication Data

US 2008/0188729 A1  Aug. 7, 2008

(30) Foreign Application Priority Data

Jan. 17, 2007 (JP) .................. 2007-008397
Dec. 21, 2007 (JP) .................. 2007-330261

(51) Int. Cl.
*A61B 5/1455* (2006.01)

(52) U.S. Cl.
USPC ........................... 600/322; 600/341; 600/310

(58) Field of Classification Search
USPC .................................. 600/309–344
See application file for complete search history.

(56) References Cited

U.S. PATENT DOCUMENTS 5,853,370 A * 12/1998 Chance et al. ............... 600/473

FOREIGN PATENT DOCUMENTS

JP   1-204657   8/1989

OTHER PUBLICATIONS

"Prefrontal activity during taste encoding: An fNIRS study" by Masako Okamoto, et al, pp. 796-806.
"Spatial and temporal analysis of human motor activity using noninvasive NIR topography" by Maki, et al.pp. 1997-2005.

* cited by examiner

*Primary Examiner* — Eric Winakur
*Assistant Examiner* — Marjan Fardanesh
(74) *Attorney, Agent, or Firm* — Mattingly & Malur, PC

(57) ABSTRACT

Appropriate measurement and analysis parameters are set according to cerebral function to be measured. To measure gustatory function, a time period of absence of cerebral activity to be measured is set so as not to contain a period of 60 seconds after start of stimulation, an activity period for analysis for an oxyhemoglobin concentration change signal is set so as to contain a period between an instant after a lapse of 16 seconds, and an instant after a lapse of 25 seconds, after the start of the stimulation, and an activity period for analysis for a deoxyhemoglobin concentration change signal is set so as to contain a period between an instant after a lapse of 28 seconds and an instant after a lapse of 37 seconds after the start of the stimulation. Moreover, a time interval between stimulations is set to 80 seconds or more.

16 Claims, 23 Drawing Sheets

FIG. 1
MOTOR AREA
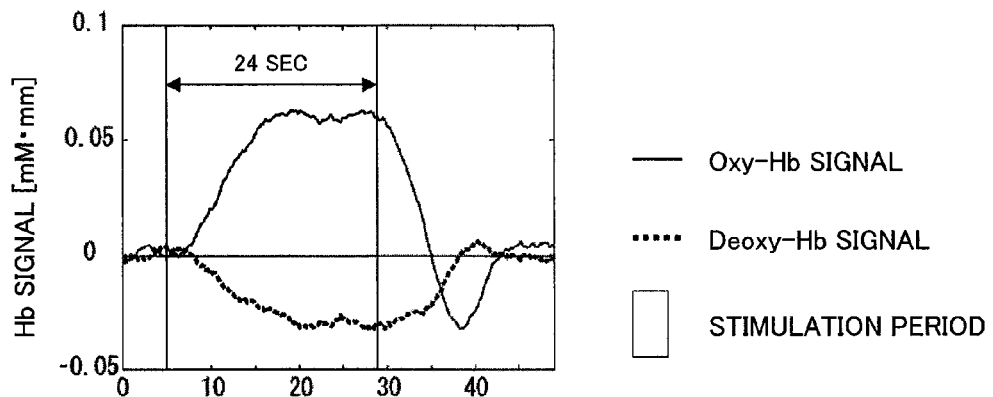
VISUAL AREA
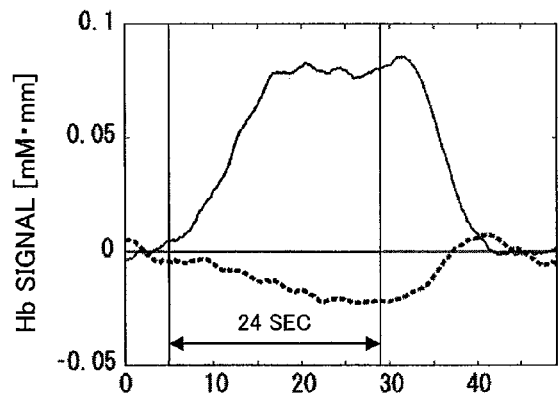
GUSTATORY AREA
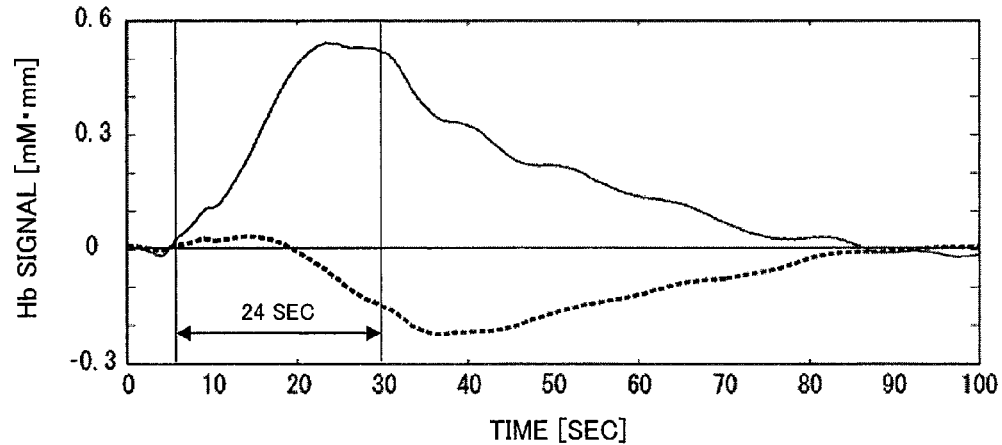

FIG. 14

| | Cerebral function to be measured | Gustatory area | | Visual area | Motor area | ·· |
|---|---|---|---|---|---|---|
| | Stimulation for measurement (Thematic test) | Aqueous solution of cane sugar | ·· | Checkerboard | Finger tapping | ·· |
| Measurement parameter | Stimulation time | 2.5 sec | ·· | 10 sec | 15 sec | ·· |
| | Interval between stimulations | 80 sec | ·· | 25 sec | 30 sec | ·· |
| | Number of repetitions | 2 times | ·· | 5 times | 5 times | ·· |
| | Others | -Dose 15 ml<br>-Concentration 20% | ·· | Switch 8 HZ | Speed 3 HZ | ·· |
| Analysis parameters | Pre-stimulation period | 5 sec | ·· | 5 sec | 5 sec | ·· |
| | Post-stimulation period | 80 sec | ·· | 20 sec | 25 sec | ·· |
| | Relaxation period | 70 sec | ·· | 15 sec | 20 sec | ·· |
| | Predicted activity period | OXY:<br>15-30 sec after start of stimulation<br>DEOXY:<br>25-50 sec after start of stimulation | ·· | | OXY:<br>10 sec after start of stimulation<br>- 8 sec after completion of stimulation<br>DEOXY:<br>15 sec after start of stimulation<br>- 8 sec after completion of stimulation | ·· |
| | Reference waveform |  | ·· | | 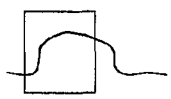 | ·· |

FIG. 20
ACTIVE WAVEFORMS IN TEMPORAL (OR BRAIN)
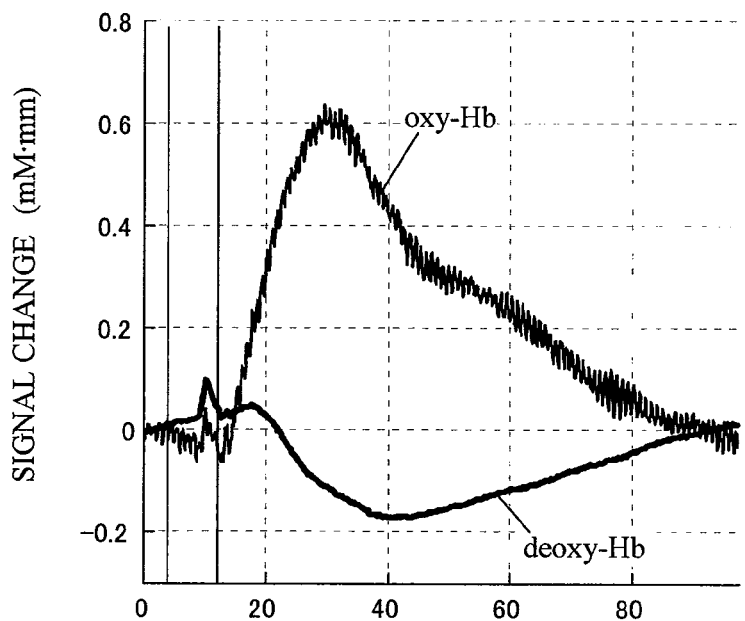
ACTIVE WAVEFORMS IN CHEEK (OR SALIVARY GLAND)
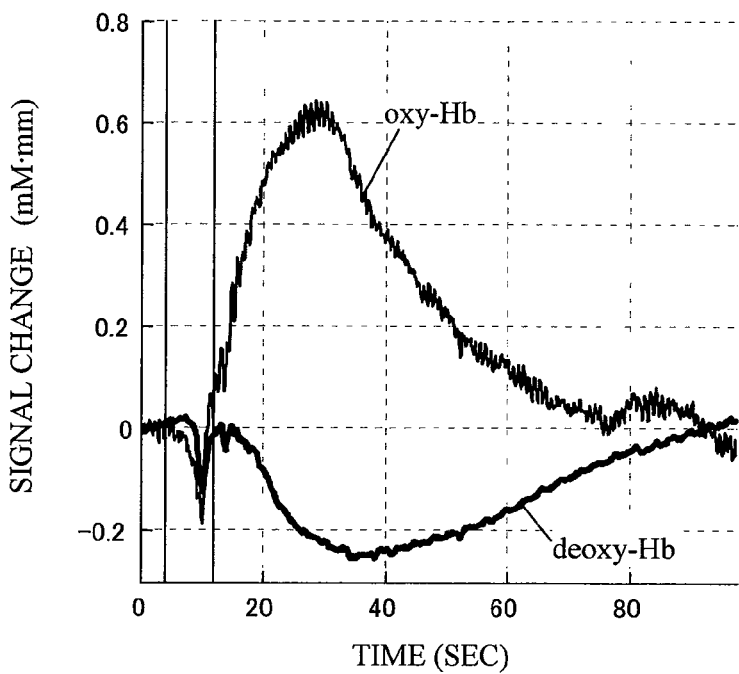

BIOLOGICAL OPTICAL MEASUREMENT INSTRUMENT

CLAIM OF PRIORITY

The present application claims priority from Japanese applications JP 2007-8397 filed on Jan. 17, 2007 and JP 2007-330261 filed on Dec. 21, 2007, the content of which is hereby incorporated by reference into this application.

BACKGROUND OF THE INVENTION

1. Field of the Invention

The present invention relates to a biological optical measurement instrument that measures biological information, specifically a signal indicative of a change in density in a light absorbing substance, by using light, and more particularly to a biological optical measurement instrument that makes cerebral activity visible by using data measured by optical biological measurement. The present invention relates also to a biological optical measurement instrument that makes visible other physiological changes, not only cerebral activity.

2. Description of the Related Art

The use of light having the peak intensity at a wavelength in a range from the visible region and the near-infrared region, and having high transmittance in vivo, makes it possible to noninvasively measure biological information. This measurement is based on Lambert-Beer's law explaining that the logarithm of a light signal measured is proportional to the product of an optical path length and a density. An extension of this law has led to development of technology for measuring a signal indicative of a relative change in concentration of hemoglobin (Hb) in vivo (hereinafter called an "Hb signal"). The Hb signals measured are of two types on "oxyhemoglobin (oxy-Hb)" and "deoxyhemoglobin (deoxy-Hb)," which will be called an "oxy-Hb signal" and a "deoxy-Hb signal," respectively. There has been a proposal of technology using the above technology for multiple measurements of the Hb signals in the human cerebral cortex and for cerebral function imaging (see Medical Physics 22, pp. 1997-2005, 1995), which is spreading out into researches and clinical practices in the field of cranial nerve science. Because of being unable to form an accurate estimate of an effective optical path length, this technology measures the Hb signals based on the relative changes, and calculates the Hb signals, using data measured during a "time period of absence of cerebral activity to be measured" (i.e., inactivity data) as the reference. In addition, to measure a physiological change other than cerebral activity, the technology calculates the Hb signals, using data measured during a "time period of absence of physiological change to be measured" as the reference. Fundamental equations for calculations will be given below.

Letting $\lambda$ be a wavelength and t be time, the intensity $T(l, t)$ of transmitted light (or the inactivity data) measured during the "time period of absence of cerebral activity to be measured" can be expressed by Equation (1):

$$-\ln[T(l,t)] = e_{oxy}(l)C_{oxy}(t)d + e_{deoxy}(l)(C_{deoxy}(t)d + a(l,t) + sc(l) \quad (1)$$

where $e_{oxy}(l)$ and $e_{deoxy}(l)$ represent molecular extinction coefficients of the oxy-Hb and the deoxy-Hb, respectively, at the wavelength $\lambda$; $C_{oxy}(t)$ and $C_{deoxy}(t)$, oxy-Hb concentration and deoxy-Hb concentration, respectively, at the time t; d, an effective optical path length; a(l, t), absorption of anything other than the hemoglobin (Hb); and sc(l), attenuation caused by scattering in vivo. On the other hand, the intensity $T^S(l, t)$ of transmitted light in the occurrence of the cerebral activity can be expressed by Equation (2):

$$-\ln[T^S(l,t)] = e_{oxy}(l)C^S_{oxy}(t)d + e_{deoxy}(l)C^S_{deoxy}(t)d + a^S(l,t) + sc^S(l) \quad (2)$$

where the superscript "S" indicates a value measured during the cerebral activity. Assuming that a light absorbing substance that undergoes changes during the cerebral activity is the hemoglobin (Hb) alone and that the absorption of anything other than the hemoglobin (Hb) and the scattering are fixed ($a(l,t)=a^S(l,t)$, $sc(l)=sc^S(l)$), subtracting Equation (2) from Equation (1) leads to Equation (3) holding:

$$-\ln[T^S(l,t)/T(l,t)] = \quad (3)$$
$$e_{oxy}(l)[C^S_{oxy}(t) - C_{oxy}(t)]d + e_{deoxy}(l)[C^S_{deoxy}(t) - C_{deoxy}(t)]d =$$
$$e_{oxy}(l)DC_{oxy}(t) + e_{deoxy}(l)DC_{deoxy}(t)$$

where $DC_{oxy}(t)=[C^S_{oxy}(t)-C_{oxy}(t)]d$ and $DC_{deoxy}(t)=[C^S_{deoxy}(t)-C_{deoxy}(t)]d$, which are defined as the oxy-Hb signal and the deoxy-Hb signal, respectively. Since it is difficult to determine the effective optical path length d, these relative signals (i.e., the oxy-Hb signal and the deoxy-Hb signal) are used to evaluate the cerebral activity. Since the light in the region visible to near-infrared for use in measurement has varying optical absorption properties depending on the oxygenated state of the hemoglobin (Hb), dual-wavelength spectrophotometry is used to derive Equation (3) for two wavelengths. This is taken as simultaneous equations, which in turn are solved to determine the oxy-Hb signal and the deoxy-Hb signal (i.e., $DC_{oxy}(t)$ and $DC_{deoxy}(t)$).

Although at the time of start of measurement (or at the period of pre-stimulation) an initial value can be simply calculated to determine the inactivity data, correction is required in order to enable detection of desired cerebral activity, because the resultant signal can possibly contain a change over a long period of time regardless of the cerebral activity.

The basic principle of this technology is to evaluate the status of cerebral activity, assuming that a local increase in the quantity of blood involved in activity of human sensory or motor function is defined as changes in the oxy-Hb signal and the deoxy-Hb signal. Typical changes involved in the cerebral activity are known as an increase in the oxy-Hb signal and a decrease in the deoxy-Hb signal. This results from an increase in the flow of blood for the purpose of compensating for oxygen and glucose consumed by metabolic activity caused by nerve activity. The increased blood is arterial blood containing oxygen, and an increase in an excessive amount of arterial blood, as compared to the amount of oxygen consumed, can possibly result in the increase in the oxy-Hb signal and the decrease in the deoxy-Hb signal. It is also generally known that such a change in the quantity of blood lags about 5 to 7 seconds behind the nerve activity. Thus, conventional researches set varying stimulations or thematic tests according to cerebral function to be measured, but nevertheless they adopt basically the same measurement paradigm and analysis method for all cerebral function to be measured from the viewpoint of time. Specifically, a general method involves setting a time interval between stimulations to about 20 to 40 seconds, and repeating the stimulation a plural number of times, thereby obtaining a cerebral activity signal, assuming that the Hb signals start changing in 5 to 7 seconds after the start of the stimulation and likewise start returning to their base lines in 5 to 7 seconds after the completion of the stimulation. This is supported by such hypothesis that "the change in the quantity of blood involved in the nerve activity occurs after a time lag of about 5 to 7 seconds behind the nerve activity." Also adopted as the analysis method is the approach of using linear data, e.g., the linear data formed by linking the average of values measured for a duration of 5 seconds before the start of the stimulation to the average of values measured for a duration of 5 seconds between the instant after a lapse of 10 seconds, and the instant after a lapse of 15 seconds, after the completion of the stimulation. Here, as "inactive condition data" for calculation, an assumption that "inactive period during which cerebral activity is assumed to be absent" is defined as a period of a few seconds before the start of the stimulation and a period after a lapse of 5 to 7 seconds after the completion of the stimulation (or equivalently, provided that inactive time parameters are set). Also when the value measured before the start of the stimulation (e.g., the average of the values measured for a duration of 5 seconds before the start of the stimulation) is used as the reference to calculate the Hb signals, base line correction using linear fitting or frequency filtering takes place. Here, the "time period of absence of cerebral activity to be measured" is defined as the period before the start of the stimulation and the period after a lapse of 5 to 7 seconds after the completion of the stimulation (e.g., provided that the average of the values measured for a duration of 5 seconds before the start of the stimulation and the average of the values measured for a duration of 5 seconds between the instant after a lapse of 10 seconds, and the instant after a lapse of 15 seconds, after the completion of the stimulation are used as the reference).

Statistical evaluation of the presence or absence of the cerebral activity, and if any, the intensity thereof requires a representative value indicative of the activity. However, also in this case, calculation has been heretofore done to determine the representative value (e.g., the average or peak of values measured for the duration between the instant after a lapse of 10 seconds, after the start of the stimulation, and the instant of completion of the stimulation). Here, it is assumed that the change with time (or the "time period of absence of cerebral activity to be measured") be defined in the same manner as above mentioned, regardless of the cerebral function to be measured (or equivalently, provided that active time parameters are set).

It has been shown that this technology enables measurement of cerebral function such as vision, motion, speech or short term memory, and the technology is widely used for clinical practices and cognitive science researches.

As for the sense of taste, cerebral function measurement using functional Magnetic Resonance Imaging (fMRI) has hitherto been the mainstream. This method involves making measurements on a subject in an unusual situation such as a case where the subject is given a sample of taste in extremely low doses through a tube put in his or her mouth with the subject fixedly placed on his or her back amid very loud noises. Besides this method, a gustatory perception evaluation apparatus using an electroencephalograph is disclosed in Japanese Patent Publication No. Hei 3-74572. There is also provided a description of a discussion on cerebral function measurement for the sense of taste, using optical biological measurement, as given in NeuroImage 31, pp. 796-806, 2006.

SUMMARY OF THE INVENTION

Cerebral function measurement technologies such as fMRI and electroencephalography cannot measure cerebral activity in gustatory area in a usual situation due to restrictions on apparatuses. The method disclosed in Japanese Patent Publication No. Hei 3-74572 can possibly obtain the result of measurement of unusual function far from the usual function of "tasting," because of requiring a mechanical device for dispensing a taste sample into the mouth as in the case of the fMRI. Further, the electroencephalography cannot determine whether the result of measurement indicates the activity in the gustatory area, because of having difficulty in identifying an active part.

On the other hand, optical biological measurement technology is expected to be used for not only conventional fundamental research but also various applications, because of having the merit of being able to measure natural cerebral function in a usual situation with a subject under noninvasive procedures and under less restraint. For example, the sense of taste and the sense of smell, in particular, are considered to depend on the surrounding situation, and hence, this technology capable of measuring the cerebral function in the usual situation can possibly achieve a high degree of effectiveness. However, there is no report on an instance of measurement using this technology of the activity in the gustatory area. The discussion given in NeuroImage 31, pp. 796-806, 2006 is focused on activity in the frontal lobe that functions to memorize taste or express it in words, not the activity in the gustatory area that reflects gustatory function. There is no detection of the activity in the generally known gustatory area region, the cause of which is not stated explicitly in the literature.

Also, optical biological measurement generally makes an attempt to measure spontaneous bloodstream fluctuations or the degree of oxygen saturation in tissue, besides the cerebral function, but the measurement makes little attempt to measure the function of an organ other than the brain. The main reason for measurement of brain function is that simple external stimulation (e.g., visual stimulation, auditory stimulation, a perceptual task, etc.) is given to produce a local change in bloodstream in a short time and hence facilitate the detection of the change. There is little discussion on other organs whose functions can be measured by use of the same approach, and thus, the possibility of measuring the functions (or equivalently, physiological changes) of other organs at varying settings of parameters is not clear.

An object of the present invention is to provide a biological optical measurement instrument capable of achieving the cerebral function measurement on the gustatory area in the usual situation, which has hitherto been difficult. An object of the present invention is also to achieve measurement of a physiological change that reflects the gustatory function, besides measurement of the cerebral function.

With respect to a conventional biological optical measurement instrument, the same approach has been adopted to measure and analyze various cerebral functions (e.g., vision, motion, speech, and so on). However, the inventors have found out that an activity signal in the gustatory area undergoes a different change with time from other typical activity signals. The present invention provides a biological optical measurement instrument having the capability of measuring the special activity signal from the gustatory area, thereby solving the foregoing problems. The inventors also have found out that light can be used to measure a physiological change that reflects the gustatory function in a salivary gland. The present invention provides a biological optical measurement instrument capable of measuring a physiological change in a salivary gland that reflects the salivary gland function, as well as the activity signal from the cerebral function, for evaluation of the gustatory function, thereby solving the foregoing problems.

Firstly, description will be given with regard to the special characteristics of the activity signal in the gustatory area. FIG. 1 shows typical activity signals in the motor area, the visual area and the gustatory area. For any of these functions, a stimulation period is set to 24 seconds. A thematic test on finger motion is used for measurement on the motor area, visual stimulation that changes between red-and-black grid patterns at 8 Hz is used for measurement on the visual area, and in-mouth stimulation, 15 milliliters of an aqueous solution of cane sugar, is used for measurement in the gustatory area. The activity signals from the motor area and the visual area are similar to each other. Specifically, the oxy-Hb signal starts increasing immediately after the start of the stimulation and reaches the vicinity of its maximum value in about 10 seconds, and the value is maintained during the stimulation period, after the completion of the stimulation, the oxy-Hb signal starts decreasing after a lapse of 0 to 5 seconds and returns to its original base line in about 5 to 15 seconds. As for the deoxy-Hb signal that decreases as opposed to the oxy-Hb signal, the deoxy-Hb signal exhibits a basically similar pattern of change with time to the oxy-Hb signal although having the characteristic of taking slightly more time to start decreasing and to reach its minimum value, and thus, the deoxy-Hb signal returns to its original base line within 15 seconds after the completion of the stimulation. On the other hand, the activity signal in the gustatory area exhibits a different pattern of change with time from the signals in the motor area and the visual area. Specifically, the oxy-Hb signal starts increasing immediately after the start of the stimulation and takes about 20 seconds to reach the vicinity of its maximum value. After the completion of the stimulation, the oxy-Hb signal takes about 60 seconds to return to its base line, and thus, it has been shown that its attenuation takes about three times more than the signals in the motor area and the visual area take. As for the deoxy-Hb signal, it reaches its minimum value in about 30 seconds after the start of the stimulation and, takes about 60 seconds after the completion of the stimulation to return to its base line, as in the case of the oxy-Hb signal.

FIG. 2 is a graph showing on the same coordinate axes the waveforms of the activity signals in the motor area, the visual area and the gustatory area. From FIG. 2, it can be seen that the waveform of the activity signal in the gustatory area is significantly different from those of the motor area and the visual area, not only in time scale but also in the magnitude of signal change. The activity signal in the gustatory area can be detected even without the use of averaging that has hitherto been necessary, since the amount of change in the waveform of the activity signal in the gustatory area is several times larger than those of the motor area and the visual area. Moreover, conventional analysis can possibly confuse the activity signal in the gustatory area with an artifact caused by bodily motion or muscular motion, since this signal is of extremely great magnitude.

It has been further found out that the activity signal in the gustatory area has the characteristic of having substantially the same active waveform regardless of the stimulation period, as shown in FIGS. 3A and 3B. A graph shown in FIG. 3A shows the Hb signals measured in an instance where a subject holds an aqueous solution of cane sugar in his or her mouth for a duration of 5 seconds and swallows it, and a graph shown in FIG. 3B shows the Hb signals measured in an instance where the subject likewise holds the aqueous solution of cane sugar in his or her mouth for a duration of 24 seconds and swallows it. In any of these instances, the oxy-Hb signal reaches the maximum amount of change in 20 to 25 seconds and the deoxy-Hb signal reaches the maximum amount of change in 30 to 35 seconds, starting at the time of start of stimulation (i.e., the time when the subject holds the aqueous solution of cane sugar in his or her mouth). This is a phenomenon that is not observed in other general cerebral functions. Active waveforms from the visual area are shown for example in FIGS. 4A and 4B. As shown in FIG. 4A, if the stimulation period is short, the Hb signals reach the maximum amount of signal change in about 10 seconds after the start of stimulation, and thereafter return to their base lines within 10 to 15 seconds. Also, the intensity of activity is low. As shown in FIG. 4B, if the stimulation period is long as opposed to the instance shown in FIG. 4A, the amount of signal change is maintained during the stimulation period, and the Hb signals return to their base lines in 10 to 15 seconds after the stimulation period.

It has been further shown that there is no big difference among individuals in the waveform of the activity signal in the gustatory area. FIGS. 5A and 5B show the average of ten cases of data measured in an instance where ten subjects hold an aqueous solution of cane sugar in their mouths for duration of 5 seconds and swallow it. FIG. 5A shows the oxy-Hb signal, and FIG. 5B shows the deoxy-Hb signal. In FIGS. 5A and 5B, an error bar represents a standard error. As indicated by the error bar, it can be seen that there is an extremely narrow range of variation among the subjects, and there is exhibited substantially the same change with time. The result of analysis of the ten cases of data has shown that the time taken for the oxy-Hb signal to reach its maximum value, after the start of gustatory stimulation, is on the average 21.0 seconds (a standard deviation of 2.0 seconds; a range of 17.8 to 23.5 seconds), and the time taken for the deoxy-Hb signal to reach its minimum value after the same is on the average 32.7 seconds (a standard deviation of 1.6 seconds; a range of 29.5 to 35.1 seconds).

Also, as shown in FIG. 19, the results of measurements made on the ears and their peripheries, as well as on the head, have shown that the same changes in the Hb signals as the waveform of the activity signal in the gustatory area are observed also on the cheekbones and in their vicinities. Here, plural small graphs shown in FIG. 19 show the changes in the Hb signals obtained by making measurements on points at intervals of 2.1 cm to 3.0 cm in the ears and their peripheries. The waveforms vary depending on the area, and, in particular, the greatest change is observed in an area around the front of each ear, (that is, in the circled parts in FIG. 19). This can be considered as a physiological change caused by the salivary gland (or equivalently, the parotid gland), not the cerebral activity signal, in view of the area. As shown in FIG. 20 and around, the changes in the Hb signals with time observed on the cheekbones and in their vicinities coincide substantially with the waveforms of the activity signals in the gustatory area (or equivalently, the brain) mentioned above.

The present invention provides a biological optical measurement instrument that sets and displays appropriate measurement and analysis methods according to cerebral function to be measured, utilizing the above findings that the activity signal in the gustatory area has the special characteristics. For example, if a "gustatory sense" is selected as the cerebral function to be measured, a time interval of 80 seconds or more between stimulations is presented and/or executed by a given means. The Hb signals in a cerebral part called the gustatory area (or a region around an operculum section and a triangular section of inferior frontal gyrus) are measured. Calculation and display of the intensity of activity or the statistical significance of the Hb signals are performed by using as an activity index an average value or a maximum value of the oxy-Hb signal measured during a period containing a given period between the instant after a lapse of 16 seconds, and the instant after a lapse of 25 seconds, after the start of the stimulation, while by using as an activity index an average value or a minimum value of the deoxy-Hb signal measured during a period containing a given period between the instant after a lapse of 28 seconds, and the instant after a lapse of 37 seconds, after the stimulation. The biological optical measurement instrument configured as mentioned above enables measurement of the cerebral activity signal in the gustatory area, which has hitherto been difficult.

The present invention also provides a biological optical measurement instrument that sets and displays appropriate measurement and analysis methods according to physiological function to be measured, utilizing the above findings that the physiological change caused by the salivary gland can be used to measure the gustatory function. Also in this case, a time interval of 80 seconds or more between stimulations is presented and/or executed by a given means. The Hb signals on the salivary gland and in its vicinity are measured. Calculation and display of the intensity of activity or the statistical significance of the Hb signals are performed by using as an activity index an average value or a maximum value of the oxy-Hb signal measured during a period containing a given period between the instant after a lapse of 16 seconds, and the instant after a lapse of 25 seconds, after the start of the stimulation, while by using as an activity index an average value or a minimum value of the deoxy-Hb signal measured during a period containing a given period between the instant after a lapse of 28 seconds, and the instant after a lapse of 37 seconds, after the stimulation. The biological optical measurement instrument configured as mentioned above enables measurement of the gustatory function.

The present invention enables high-sensitivity measurement of the cerebral activity signal in the gustatory area, which has been impossible with the conventional method. The present invention also enables measurement of the physiological change caused by the salivary gland and thereby enables multiple evaluation of various aspects of the gustatory function. The present invention greatly reduces the required number of averaging calculations than hitherto, because of being able to obtain the cerebral activity signal several times to about ten times greater than the cerebral activity signal measured by the conventional biological optical measurement instrument. The present invention enables more practical and accurate evaluation of gustatory function, because of being able to evaluate cerebral activity coincident with usual eating and drinking (e.g., usual action, quantity and taste), which has been impossible with other cerebral function measurement instruments. Moreover, the present invention is applicable to an assist tool for diagnosis or treatment of gustatory disorders, or development and evaluation of drinks or foods.

BRIEF DESCRIPTION OF THE DRAWINGS

FIG. 1 is graphs showing typical activity Hb signals in the motor area, the visual area and the gustatory area respectively.

FIG. 14 is a table showing an example of various parameters corresponding to cerebral function and stimulation for measurement.

FIG. 20 is graphs showing comparison of Hb signals observed on cheekbones and in their vicinities and the waveforms of the activity signals in the gustatory area (or equivalently, the brain).

DETAILED DESCRIPTION OF THE PREFERRED EMBODIMENTS

Figure 2:
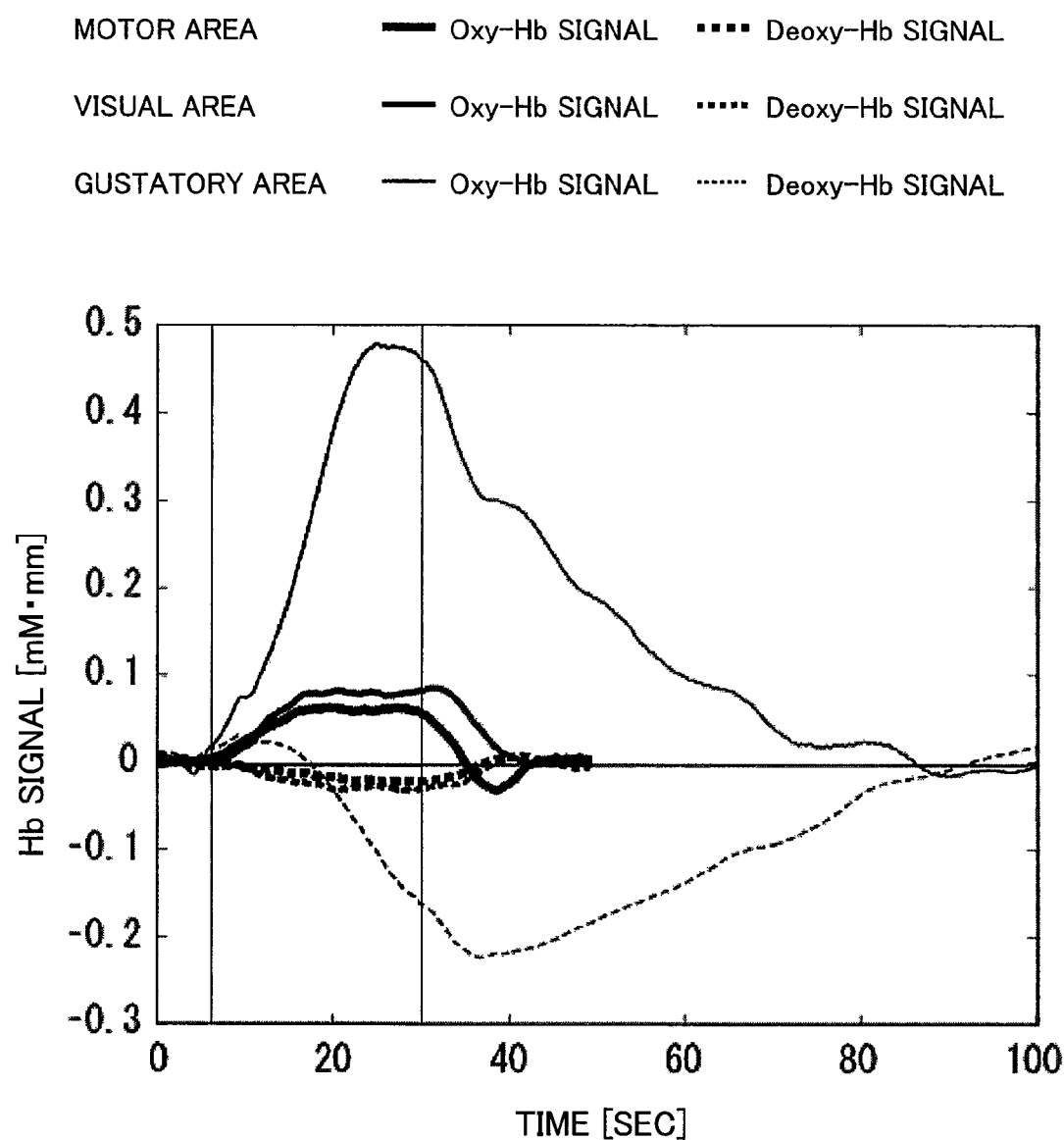
FIG. 2 is a graph showing on the same scale the typical activity Hb signals in the motor area, the visual area and the gustatory area.
Figure 3A:
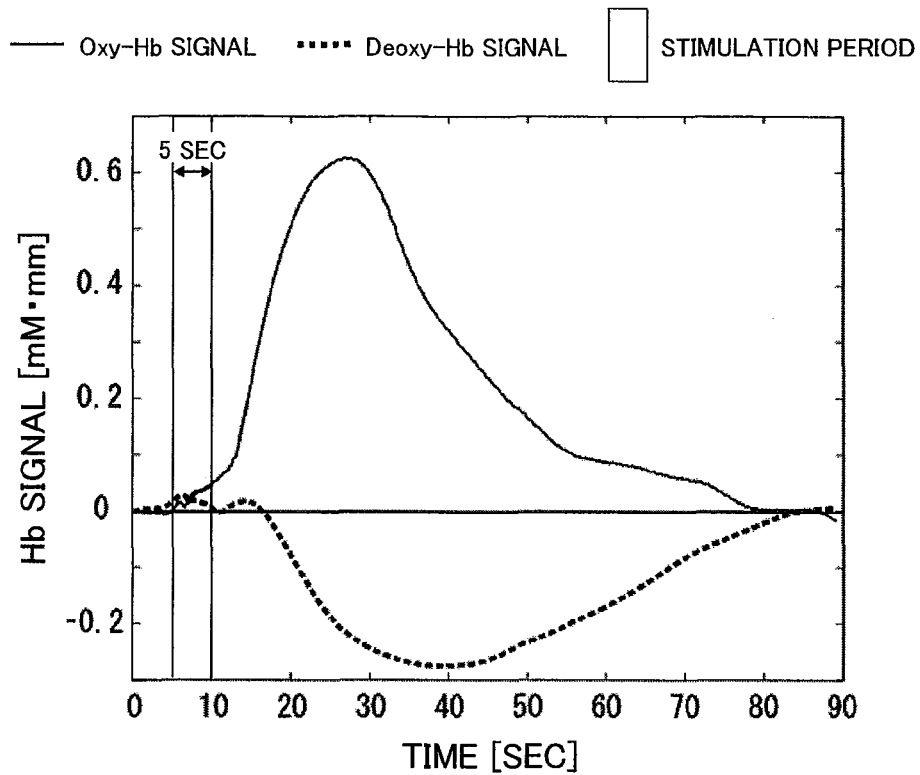
FIGS. 3A and 3B are graphs showing the activity Hb signals in the gustatory area measured during different stimulation periods.
Figure 3B:
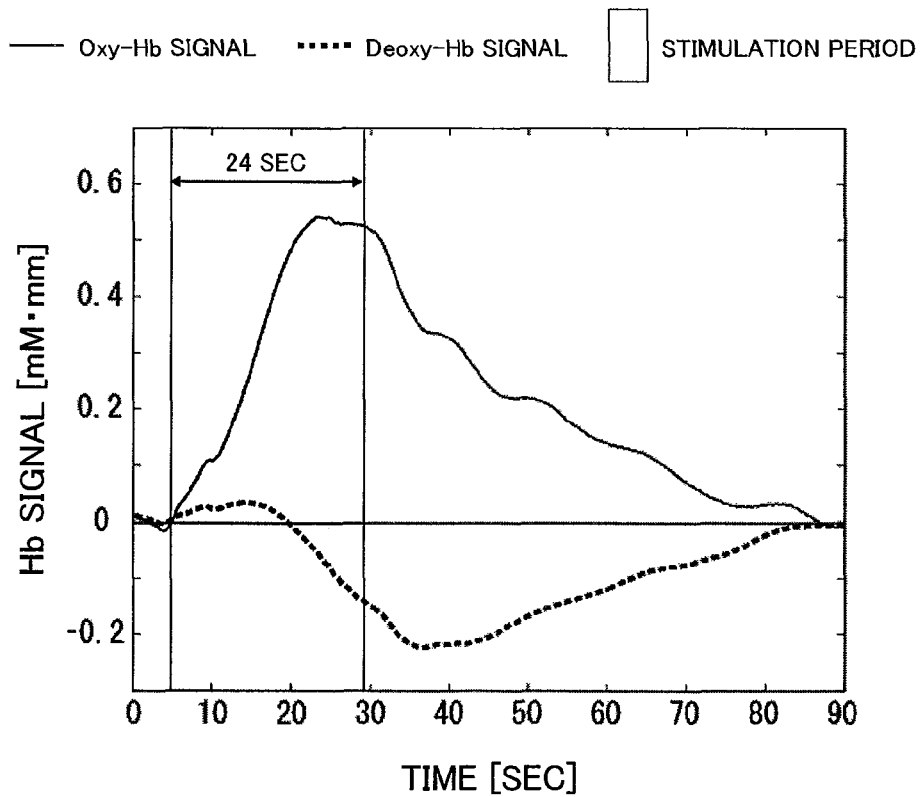

Description will be given below with regard to embodiments of the present invention.

First Embodiment

A basic embodiment for carrying out the present invention will be described with reference to FIGS. 6, 7, 10 and 12. FIGS. 6, 7, 10 and 12 show a common block diagram showing in schematic form a biological optical measurement instrument according to the present invention.

An optical biological measurement unit includes a control unit 602 configured of an electronic computer typified by a personal computer or a workstation, two laser diodes 608 and 609 having different peak wavelengths, oscillators 606 and 607 that generate signals for modulating the two laser diodes with different frequencies, a photocoupler 610 that couples together two light beams having the different peak wavelengths, a light irradiation means for irradiating a subject at a point of light irradiation thereon with the light from the photocoupler 610 via an optical fiber 612, a photodetector 611 that detects the coupled light via an optical fiber 613 at a point of light detection spaced appropriately away from the light irradiation means (e.g., a point spaced about 3 cm apart, as employed in the first embodiment), lock-in amplifiers 604 and 605 supplied with inputs of the modulated frequencies from the oscillators with the frequencies acting as reference signals, and an analog-to-digital converter 603 that converts transmitted-light signals on the light in the wave bands of frequencies, outputted by the lock-in amplifiers, from the analog ones to the digital ones. The center of a point of measurement coincides substantially with the midpoint between the point of light irradiation and the point of light detection.

In FIGS. 6, 7, 10 and 12, the numbers of points of light irradiation, points of light detection and points of measurement are shown as being only one each. However, plural points of light irradiation and points of light detection may be actually disposed as alternating with each other, to thereby set plural points of measurement. The instrument of the present invention can use a single detector to measure light signals in plural points, because of using the oscillators to separate plural light signals. Although the first embodiment uses the oscillators to separate the plural light signals, pulse light may be used to separate the light signals in accordance with the timing of turn-on without the use of the oscillators.

The transmitted-light signals on the light in the wave bands of frequencies are subjected to analog-digital conversion by the analog-to-digital converter 603 and then inputted to and stored in the control unit 602. The control unit 602 calculates each Hb signals in each measured parts, on the basis of the transmitted-light signals, and stores the Hb signals together with the original signals (or the transmitted-light signals). A method for calculating the Hb signals in the transmitted-light signals is described in detail in Medical Physics 22, pp. 1997-2005, 1995. Although the control unit 602, as employed in the first embodiment, is described as performing both measurement control and data storage and analysis, a control unit and an analyzer may be provided separately to perform the control and the analysis, respectively, on different PCs.

The control unit 602 has different features in two functions, namely, a presentation function for measurement method and a data analysis function, from the prior art.

Presentation Function for Measurement Method

Firstly, description will be given with reference to FIGS. 6 and 7 with regard to the presentation function for measurement method. A measurer first selects cerebral function to be measured on display screens 601 and 701. A "gustatory sense" radio button is selected on the display screen 601 as shown for example in FIG. 6, and a "visual sense/others" radio button is selected on the display screen 701 as shown for example in FIG. 7. Incidentally, it is to be understood that a graphical user interface shown in FIGS. 6 and 7 is illustrative only, and the present invention is not limited to this embodiment.

Figure 6:
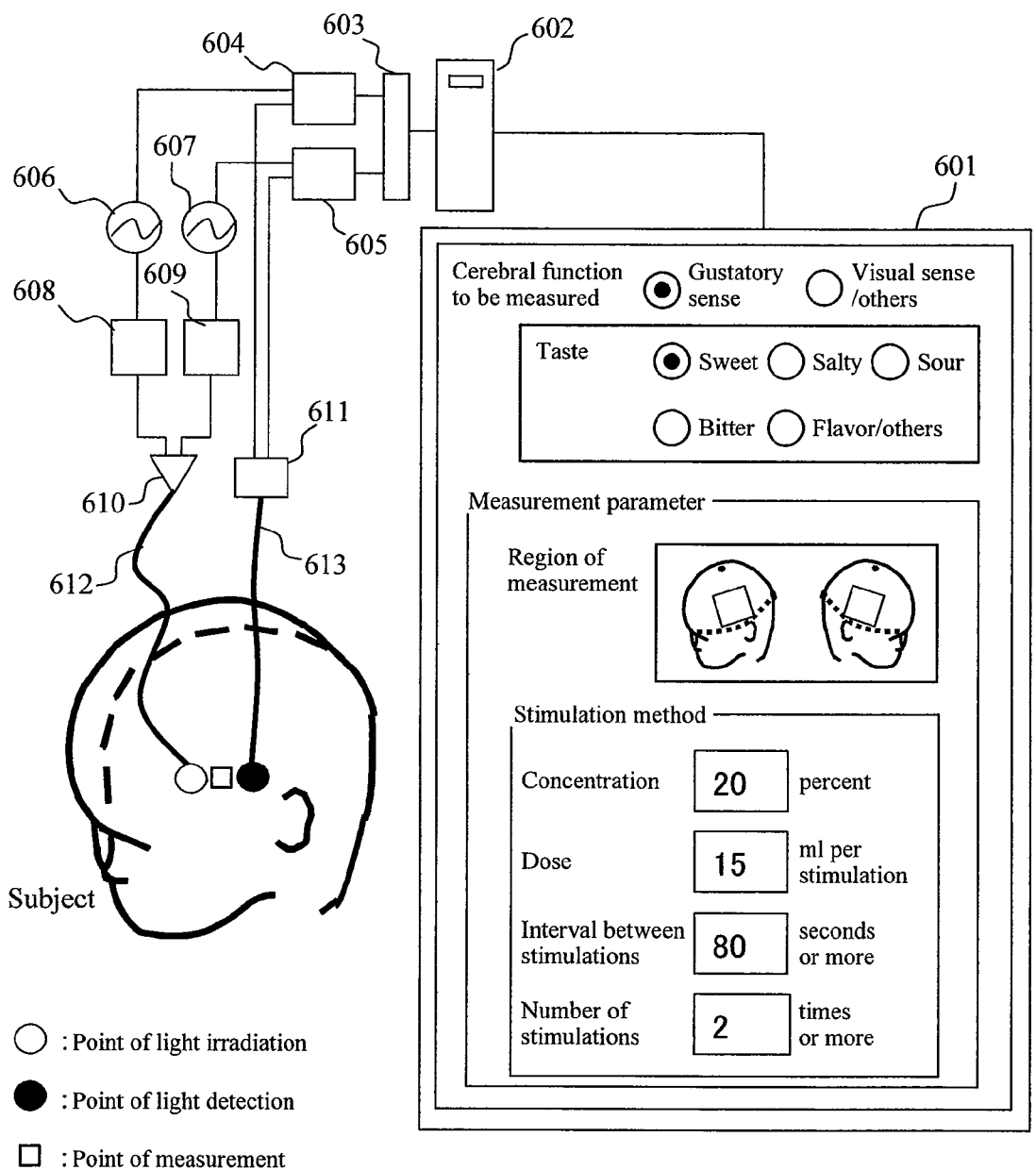
FIG. 6 is a block diagram showing the configuration of an instrument according to one embodiment of the present invention.
Figure 7:
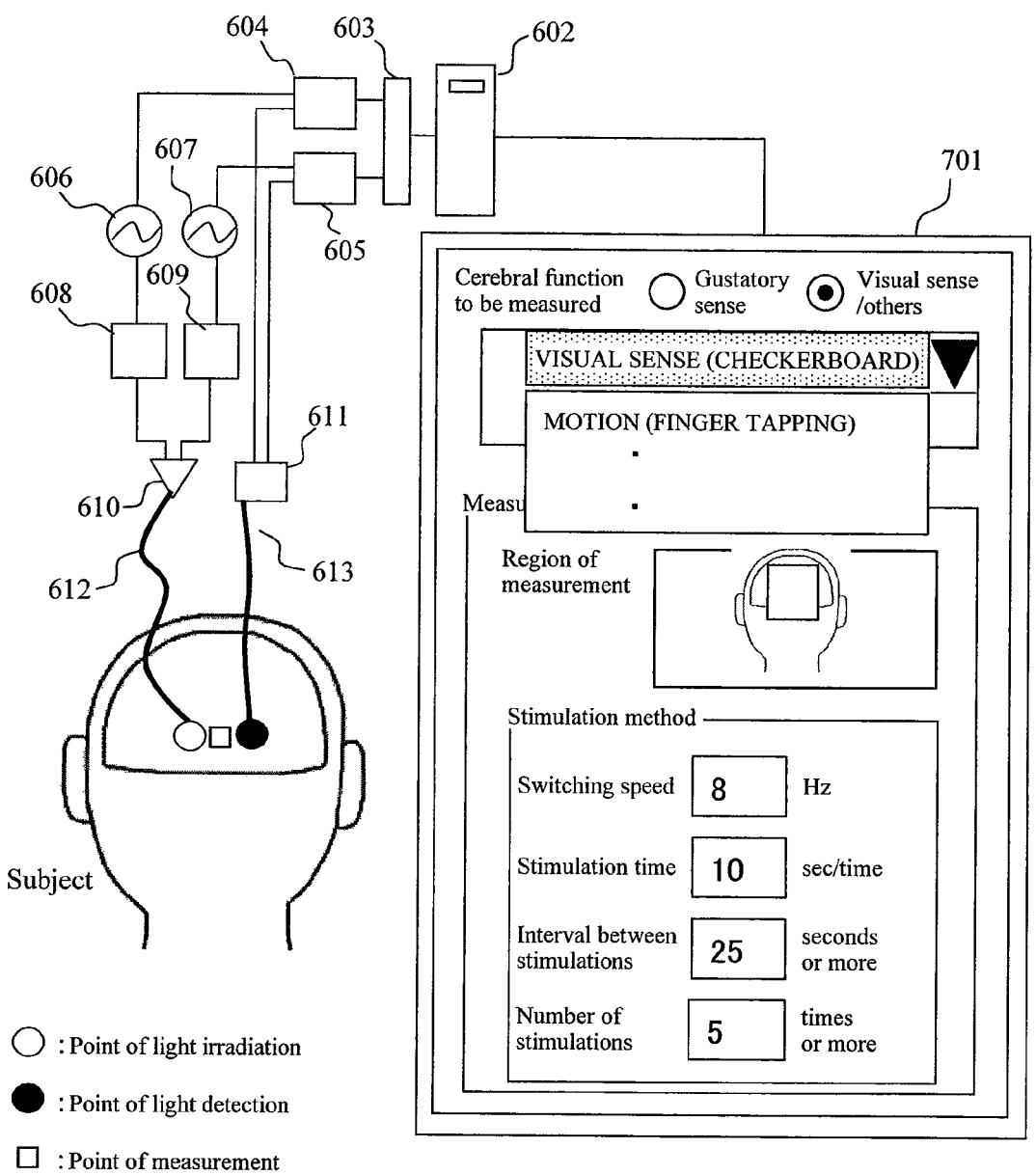
FIG. 7 is a block diagram showing the configuration of an instrument according to one embodiment of the present invention.
Figure 8:
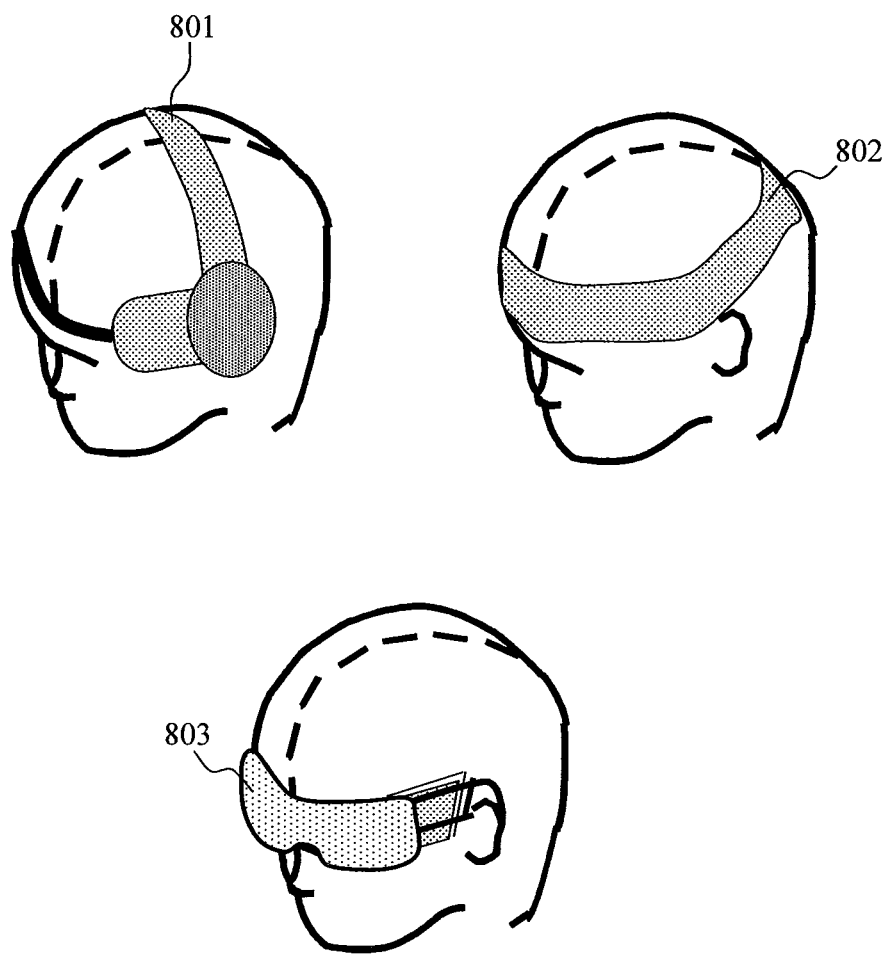
FIG. 8 is an illustration showing examples of subject interfaces (or measurement probe holders) for gustatory area measurement.

For "gustatory sense" measurement shown in FIG. 6, radio buttons for specific selection of the type of taste to be next presented are displayed. When a sweet taste is selected as the taste to be presented, a next measurement parameter list is displayed. A minimum required region of measurement, around the temple that covers an operculum section, an island, which is known as a primary gustatory area, and so on, is first displayed. Examples of measurement interfaces that cover the region of measurement are shown in FIG. 8. In FIG. 8, a headphone type 801, a headband type 802 and a spectacles type 803 are shown as probe caps specialized for gustatory area measurement. All these types are configured to be able to make a measurement on the temple and its vicinity including the primary gustatory area, and are also characterized by having such shapes as may not impede the usual actions of "drinking" and "eating." Further, the measurement parameter list on the display screen 601 contains some kinds of presenting stimulation, such as an appropriate concentration of a sweet taste sample (e.g., the concentration of an aqueous solution of glucose, cane sugar, sugar, an artificial sweetener, or the like), a dose of the sample per stimulation, an interval between stimulations, and the number of stimulations. Of the parameters for the gustatory sense measurement, the time interval between stimulations is most clearly distinct from the time intervals for other function measurements. The time interval between stimulations is set to "80" seconds or more, since an activity signal in the gustatory area takes about 80 to 90 seconds to return to its base line value (provided that the stimulation start time is taken as 0 second), as shown in FIGS. 1 and 2. Moreover, a small number of repetitions of the same stimulation can be set since the amount of change in the activity signal in the gustatory area is several times larger than the amount of change in a conventional cerebral activity signal (see FIG. 2). Although the number of stimulations is set to "two" times or more as shown in FIG. 6, the number of stimulations may be one. These measurement parameters are stored in a memory of the control unit 602, and are displayed as default values on the display screen 601 if the gustatory sense is selected as the cerebral function to be measured.

Figure 21:
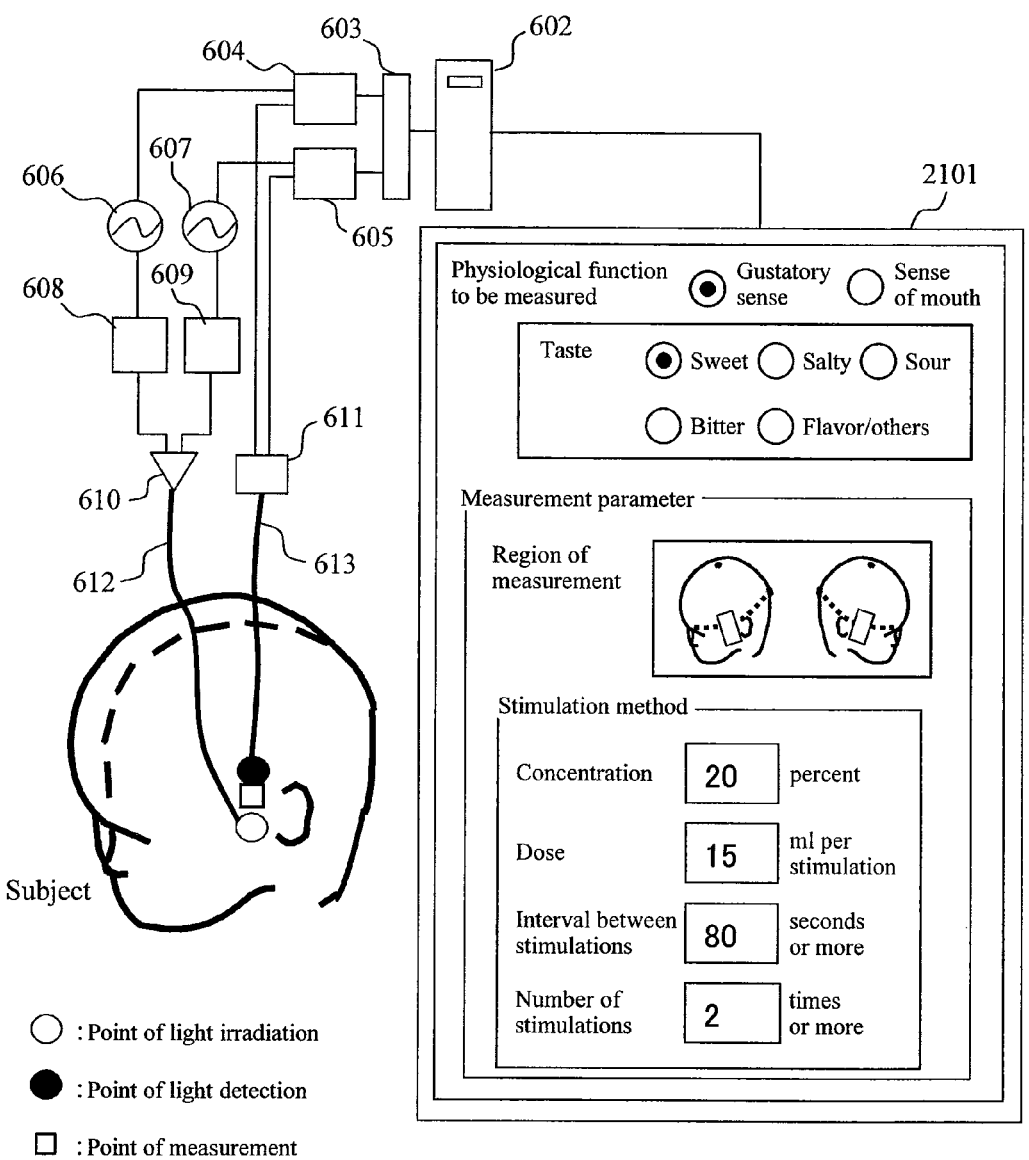
FIG. 21 is an illustration showing an example of an input screen for measurement parameters for gustatory function measurement.
Figure 22:
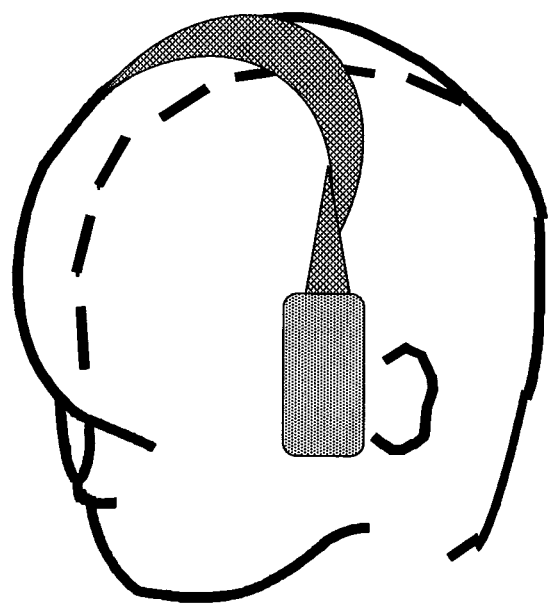
FIG. 22 is an illustration showing an example of a subject interface that covers a region of measurement.

If gustatory function is selected, parameters for measurement of a physiological change caused by a salivary gland, besides the parameters for cerebral activity measurement, can be also displayed as shown in FIG. 21. On this occasion, the parameters displayed on a display screen 2102 are basically the same as the parameters for cerebral activity measurement shown in FIG. 6, except display of a region that covers the salivary gland, rather than the gustatory area, as display of a region of measurement. An example of a subject interface that covers the region of measurement, which is used if the salivary gland is selected as the region of measurement, is shown in FIG. 22. In FIG. 22, a headphone type is shown as a probe cap specialized for salivary gland measurement. This type is of an effective shape for measurement on cheekbones and their vicinities, containing a parotid gland.

Figure 9:
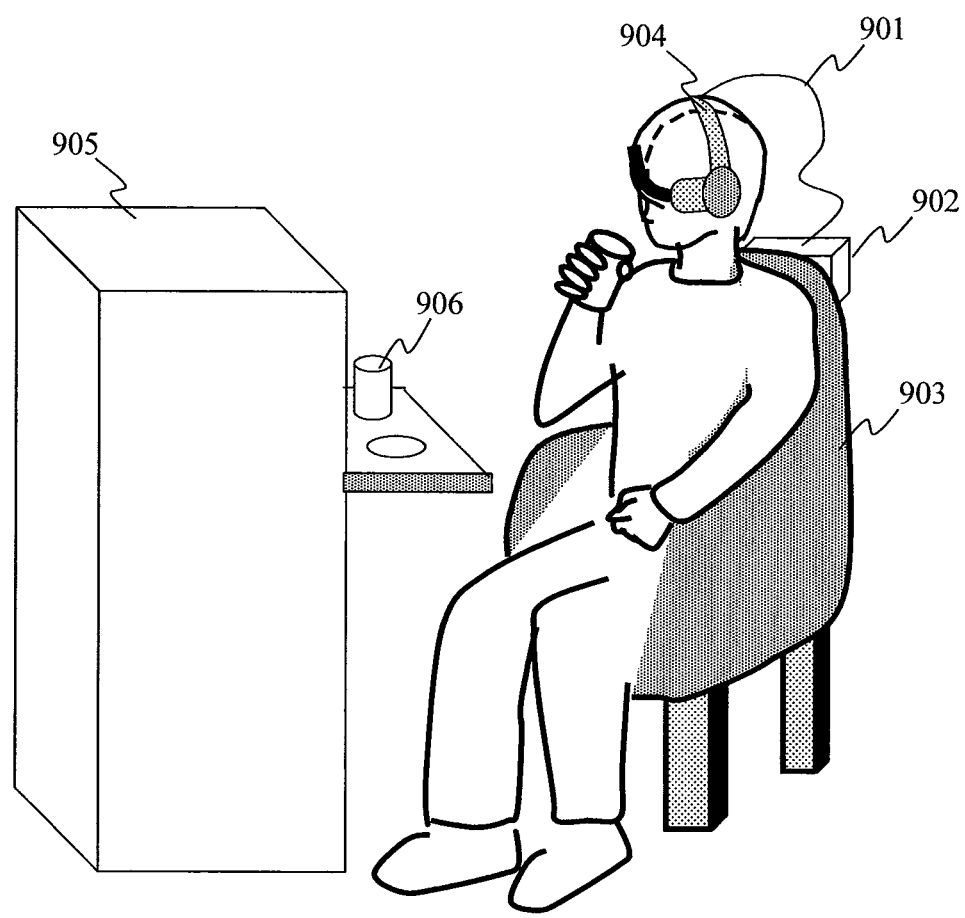
FIG. 9 is a conceptual illustration of a totally automated gustatory function measurement system.

In the first embodiment, the measurement parameter list is displayed on the screen to assist the measurer to carry out a measurement. Besides this method, the parameters may be inputted into a stimulation system for execution of actual stimulation. For example, the function of presenting the timing of stimulation (or the timing of intake of a taste sample) in image or voice form in accordance with the measurement parameters increases automation of measurement and hence reduces loads on the measurer. FIG. 9 shows a conceptual illustration of a totally automated gustatory function measurement system. A headphone type probe holder 904 configured to make a measurement on the gustatory area, which a subject wears, is connected via an optical fiber 901 to a measurement box 902, which in turn records measured transmitted-light data. The measurement box 902 may be attached to the subject or be integral with a measurement chair 903. The measurement box 902 or the measurement chair 903 integral with the measurement box has the capability of wire or radio communication with a biological optical measurement instrument body 905. The biological optical measurement instrument body 905 performs all of the following operations: execution of a measurement paradigm, storage and analysis of a measured signal, and display of results. For example, a taste sample to be next presented, the taste, dose and timing of which are set, can be poured directly into a cup 906 for presentation. After taking a presented drink at the presented timing and in the presented way, the subject can see the activity signal in his or her own gustatory area in image, graphical or numerical form or in other forms.

Incidentally, this gustatory function measurement system can be likewise used to measure the gustatory function, based on the physiological change caused by the salivary gland, rather than the gustatory area.

When the "visual sense/others" radio button is selected as the cerebral function to be measured on the display screen 701 as shown for example in FIG. 7, the cerebral function to be measured is specifically selected from a pop-up menu. When a "visual sense (checkerboard)" is selected as shown in FIG. 7, the occipital lobe that serves as visual function is displayed as a part to be measured. Further, detailed ways of checkerboard stimulation, such as a switching speed, a stimulation time, a time interval between stimulations, and the number of stimulations, are displayed. Similar to the case where the gustatory sense" radio button is selected, in the case the "visual sense/others" radio button is selected, the measurement parameter list may be entered as set parameters into the stimulation system for use in actual stimulation. When the "visual sense/others" radio button is selected, a cerebral function measurement method using a conventional biological optical measurement instrument is adopted. The main points of difference between the parameters for "visual sense/others" measurement and the parameters for the gustatory area measurement are that a time interval of about 20 to 60 seconds between stimulations is sufficient in the "visual sense/others" measurement, and that the number of repetitions of the stimulation must be set to three times or more (e.g., "five" times or more as shown for example in FIG. 7) for the "visual sense/others" measurement because of low signal intensity thereof.

Data Analysis Function

Description will now be given with regard to a data analysis function with reference to FIGS. 10, 11, 12 and 13.

Figure 10:
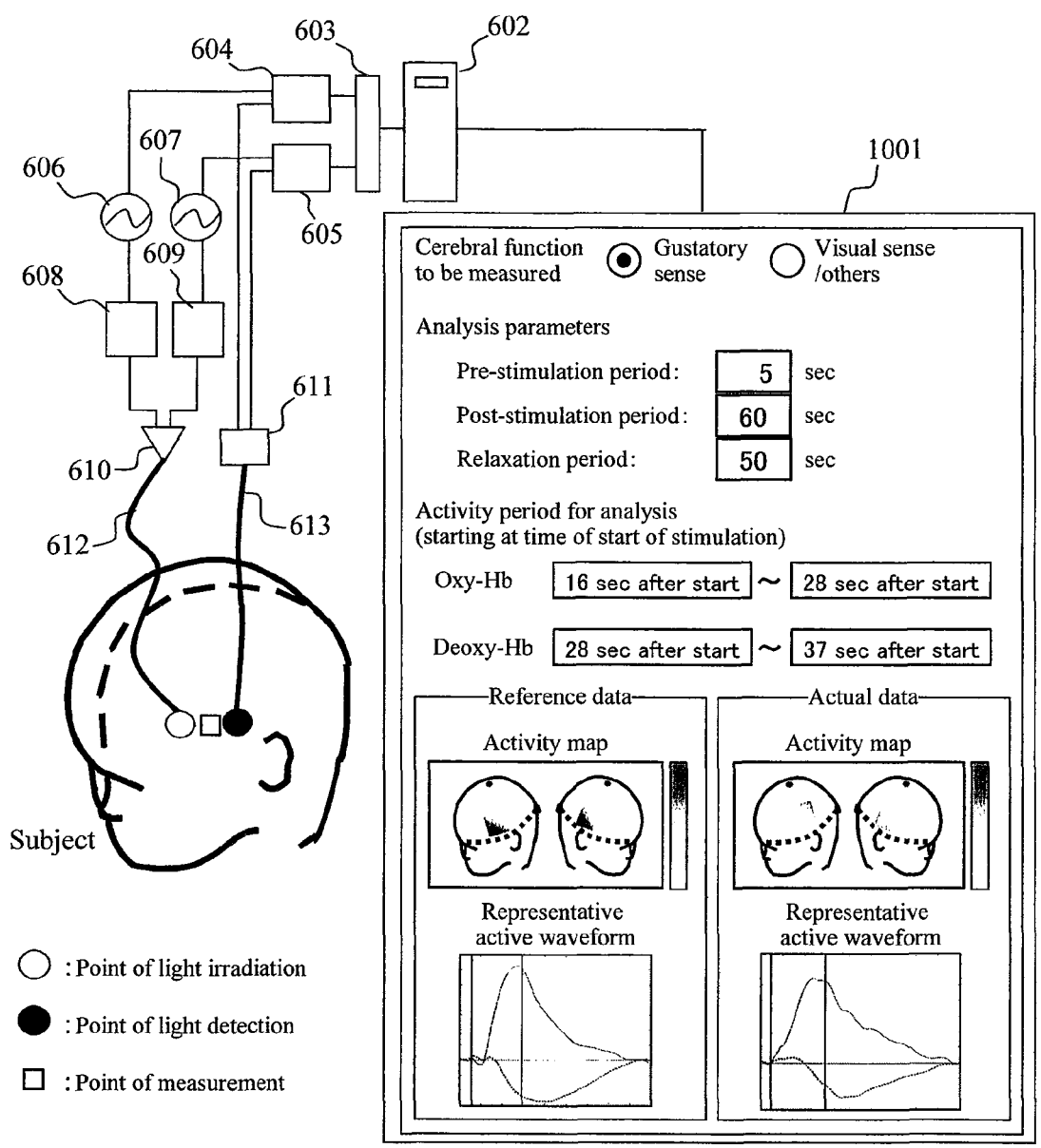
FIG. 10 is a block diagram showing the configuration of an instrument according to one embodiment of the present invention.
Figure 11:
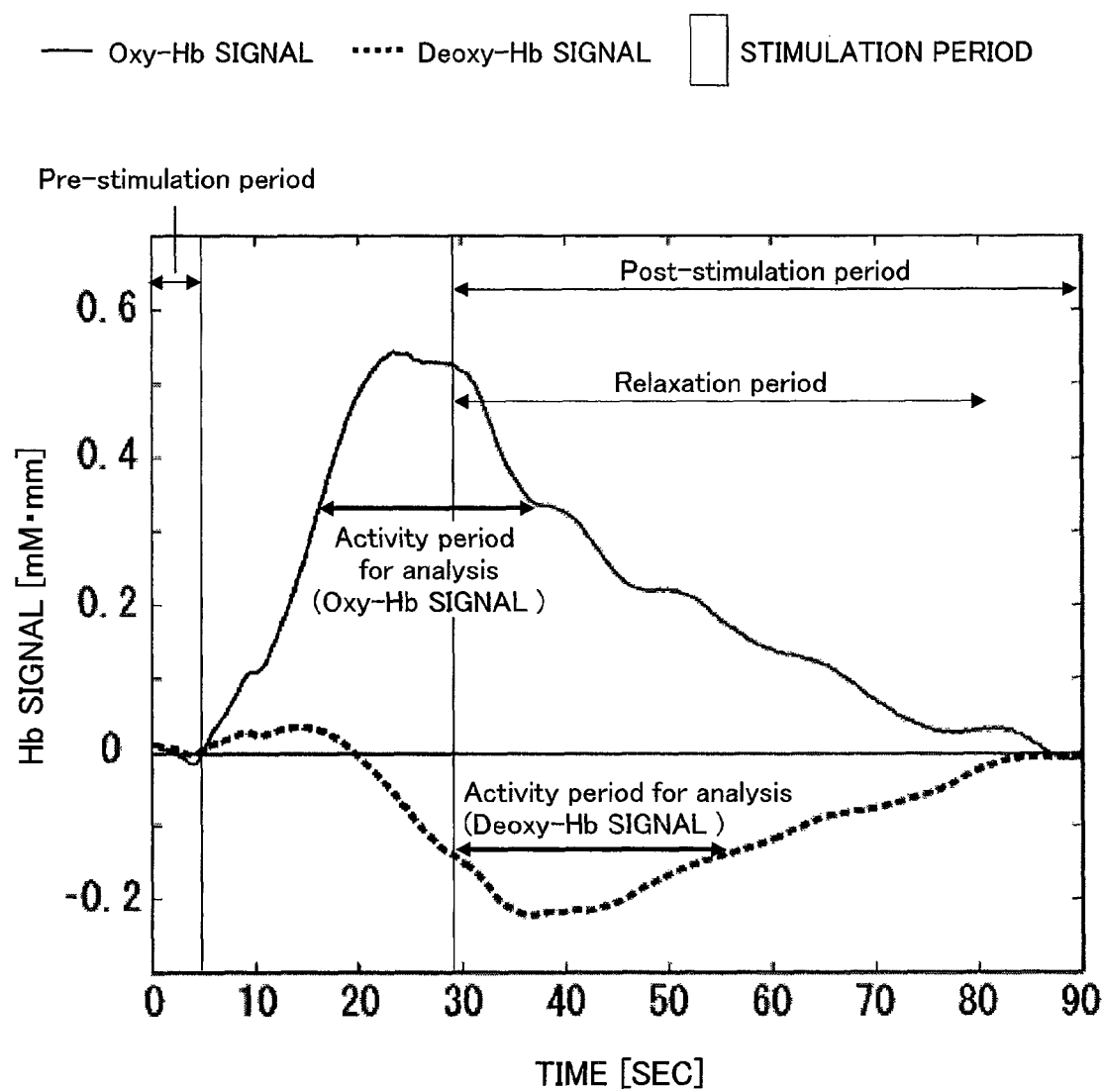
FIG. 11 is a graph showing an example of the Hb signals in the gustatory area.

FIGS. 10 and 11 show an example of data analysis in an instance where the "gustatory sense" is selected as the function to be measured. First, a "pre-stimulation" period, a "post-stimulation" period and a "relaxation" period must be set in order to set the range of data analysis focusing on a stimulation period (see FIGS. 11 and 13). The pre-stimulation period is the period before stimulation, which is set in order to obtain a change caused by the stimulation, and this period is not particularly limited in length. Since, if the stimulation is repeated, a change caused by the previous stimulation can possibly remain depending on the length of the time interval between stimulations, it is desirable that the pre-stimulation period be set as short as possible (typically about 1 to 10 seconds) in order to avoid the influence of the change. The pre-stimulation period is set to "5" seconds as shown for example in FIG. 10. The post-stimulation period is an important parameter for the present invention. The post-stimulation period represents the period for analysis after the completion of the stimulation, and this period must be set longer than the periods for other cerebral functions, because the activity of the gustatory area takes 80 to 90 seconds after the start of the stimulation, as shown in FIGS. 1 and 2. As shown for example in FIG. 10, the post-stimulation period is set to 60 seconds (or equivalently, a time interval of 84 seconds between stimulations, starting at the start of the stimulation), since the stimulation period is set to 24 seconds. The relaxation period is used to eliminate long-term fluctuation components changing regardless of the stimulation. For example, linear fitting based on the average of values measured during the pre-stimulation period and the average of values measured during the post-stimulation period except the relaxation period is performed for base line correction. As shown for example in FIG. 10, the relaxation period is set to "50" seconds in order to avoid as much as possible the period in which a change in signal remains. Moreover, frequency filtering (e.g., the cutting of low-frequency components) with regard to the entire time period between the pre-stimulation period and the post-stimulation period may be used for base line correction. Moreover, a method may be adopted which involves simultaneously measuring a cerebral activity signal in an area other than the gustatory area, such as the activity of the motor area caused by the "drinking" action, and correcting the cerebral activity signal, on the basis of the intensity of activity measured. Further, a method not using the first reaction for analysis is effective because the gustatory area measurement has obtained the result of observation of an instance where a reaction to the first stimulation is extremely strong. Moreover, a method may be adopted which involves evaluating the first activity signal alone to thereby evaluate sensitivity to taste, as opposed to the above.

Figure 5A:
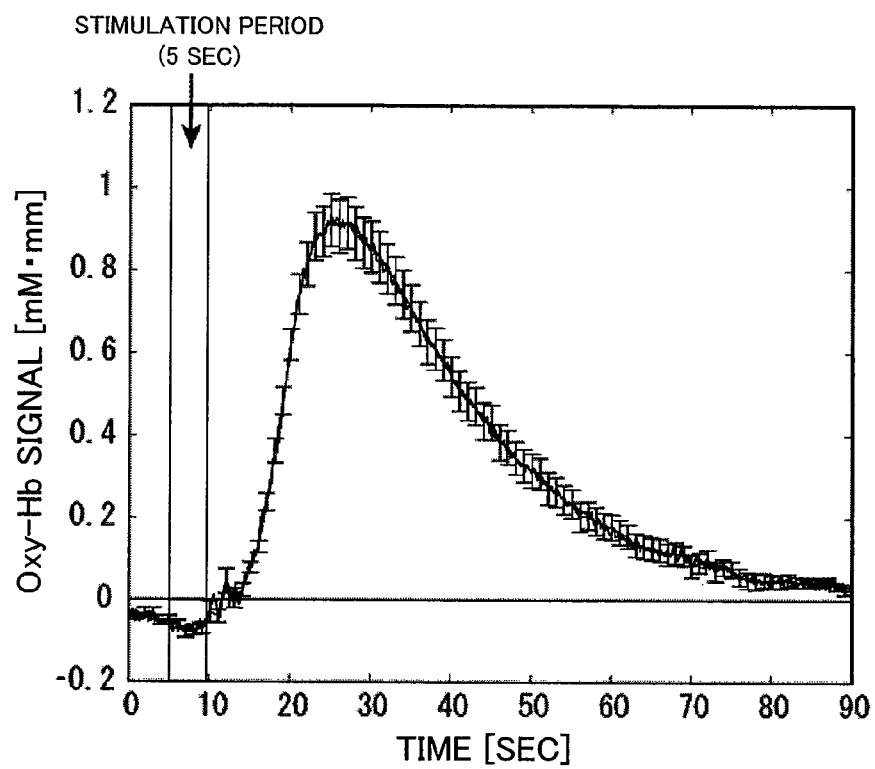
FIGS. 5A and 5B are graphs showing the average of the activity signals in the gustatory areas of ten subjects, showing an oxy-Hb signal and a deoxy-Hb signal, respectively.
Figure 5B:
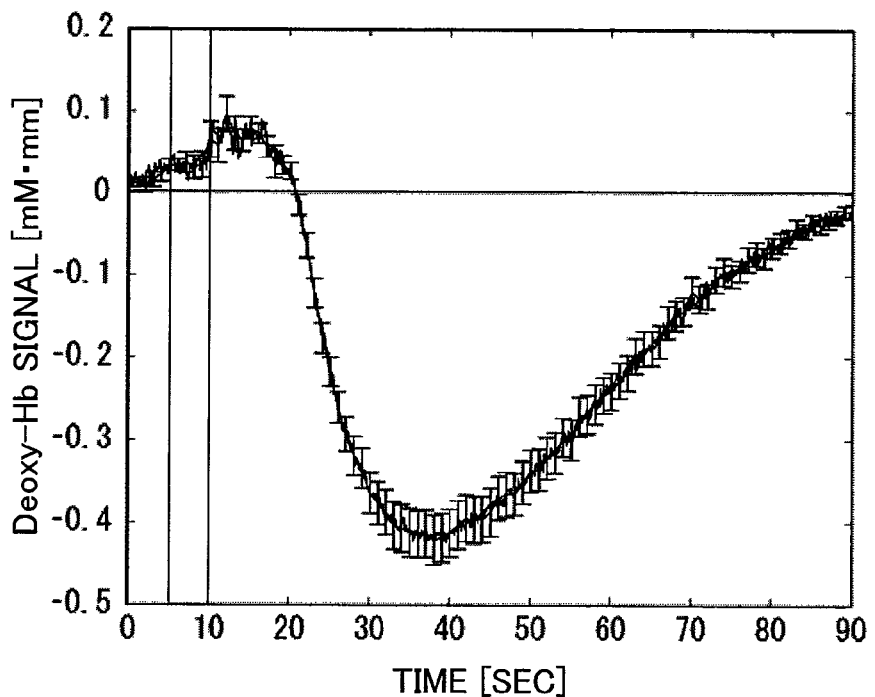

FIG. 10 further shows a parameter setting screen for use in evaluation of changes in Hb signals caused by stimulation. An activity period for analysis is set as shown for example in FIG. 10. The activity period for analysis is for the purpose of evaluating the presence or absence of the cerebral activity, and if any, the intensity thereof on the basis of the amount of signal change during this period, and thus, the activity period having the highest reliability and validity must be set as the activity period for analysis. As shown in FIGS. 5A and 5B, the result of analysis of the average activity signal in the gustatory area has shown that, after the start of gustatory stimulation, the time taken for the oxy-Hb signal to reach its maximum value is on the average 21.0 seconds (a standard deviation of 2.0 seconds; a range of 17.8 to 23.5 seconds), and the time taken for the deoxy-Hb signal to reach its minimum value is on the average 32.7 seconds (a standard deviation of 1.6 seconds; a range of 29.5 to 35.1 seconds). Thus, as an example, the period between the instant after a lapse of 16 seconds, and the instant after a lapse of 25 seconds, after the start of the stimulation is set as the activity period for analysis for the oxy-Hb signal, while the period between the instant after a lapse of 28 seconds, and the instant after a lapse of 37 seconds, after the start of the stimulation is set as the activity period for analysis for the deoxy-Hb signal. For example, the average value or the peak value measured during the activity period for analysis, or the result of statistical analysis such as t-test or analysis of variance using these values is displayed on an activity map or the like. Alternatively, an activity evaluation method based on typical active waveforms shown in FIGS. 5A and 5B is also effective. Also in this case, since a general hemodynamics function for use in fMRI analysis or the like cannot detect the activity signal in the gustatory area found by the inventors, a polynomial function as shown in FIGS. 5A and 5B, in which the oxy-Hb signal has the maximum value in the period between the instant after a lapse of 16 seconds, and the instant after a lapse of 25 seconds, after the start of the stimulation, while the deoxy-Hb signal has the minimum value in the period between the instant after a lapse of 28 seconds, and the instant after a lapse of 37 seconds, after the start of the stimulation, is used as the reference waveform. A template waveform theoretically created from instances of researches, an average waveform created from a database having actual data stored therein, or the like is used as the reference waveform. Moreover, the waveform of data to be analyzed is subjected to appropriate filtering for use, depending on according to the data to be analyzed. These reference waveforms are utilized for correlation analysis or analysis using a general linear model. Further, a time constant (as defined for example as $e^{-u*t}$) of an attenuation curve may be used as an index for activity evaluation, because the waveform of the activity signal in the gustatory area is characterized in that, after the peak, the time for attenuation of the signal is more than that of other cerebral function activity signals.

The result of analysis is shown in the form of, for example, the activity map or the active waveform. Besides the simple amount of signal change, a statistical value typified by the t value, the F value, the p value or the like, the time constant of the attenuation curve, a correlation coefficient, or the like can be used for the activity map. Of course, not only parametric analysis but also nonparametric analysis can be used. Moreover, a representative active waveform indicates a waveform measured at a single point of measurement where activity is most noticeable, or the average of waveforms measured at plural points of measurement in an activity region. In these cases, the approach of displaying side by side "reference data" indicative of predicted results and "actual data" actually measured is used to facilitate comparison. Average data on the same subject previously measured, average data on subjects, or ideal activity data theoretically derived, or the like can be used as the "reference data."

Figure 23:
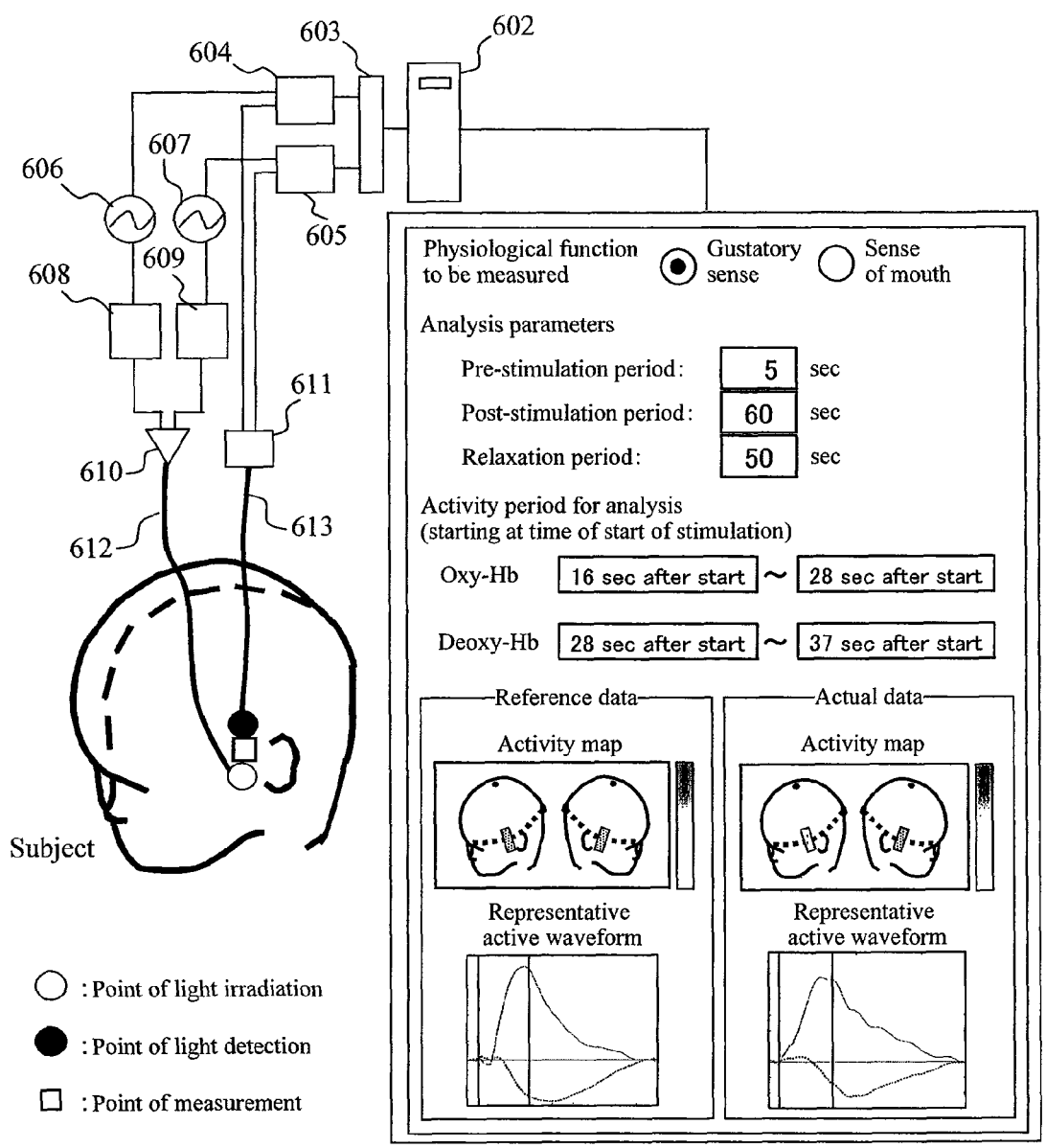
FIG. 23 is an illustration showing an example of a parameter setting screen for data analysis.

FIG. 23 shows a parameter setting screen for data analysis for gustatory function measurement based on the physiological change caused by the salivary gland. In this case, substantially the same parameter values as that for analysis of gustatory area function are set for the pre-stimulation period, the post-stimulation period, the relaxation period, and the activity period for analysis respectively, for the same reason for analysis of gustatory area function described above. For example, the activity period for analysis for an oxyhemoglobin concentration change signal is set so as to contain a period between the instant after a lapse of 16 seconds, and the instant after a lapse of 25 seconds, after the start of the stimulation, while the activity period for analysis for a deoxyhemoglobin concentration change signal is set so as to contain a period between the instant after a lapse of 28 seconds, and the instant after a lapse of 37 seconds, after the start of the stimulation. An average value or a maximum value of the oxyhemoglobin concentration change signal or the deoxyhemoglobin concentration change signal measured during the activity period for analysis is used to evaluate the presence or absence of the physiological change or the intensity thereof. The analysis parameters include reference waveform data on the physiological change, for evaluation of the presence or absence of the physiological change or the intensity thereof. The reference waveform data for the oxyhemoglobin concentration change signal is a polynomial function having a maximum value in the period between the instant after a lapse of 16 seconds, and the instant after a lapse of 25 seconds, after the start of the stimulation, while the reference waveform data for the deoxyhemoglobin concentration change signal is a polynomial function having a minimum value in the period between the instant after a lapse of 28 seconds, and the instant after a lapse of 37 seconds, after the start of the stimulation.

Figure 4A:
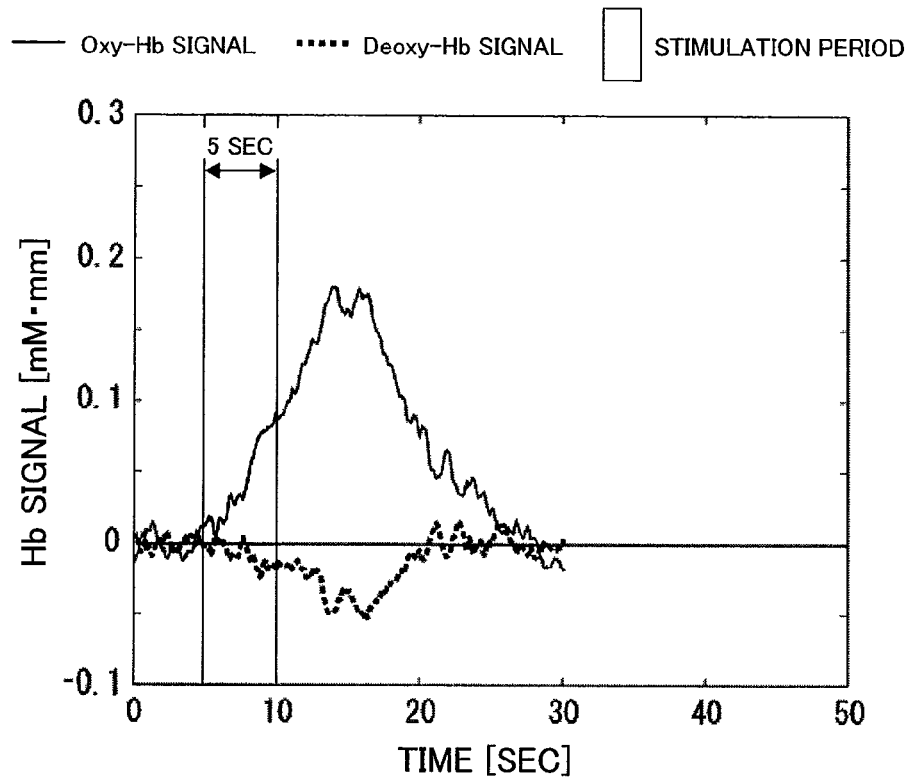
FIGS. 4A and 4B are graphs showing the activity Hb signals in the visual area measured during different stimulation periods.
Figure 4B:
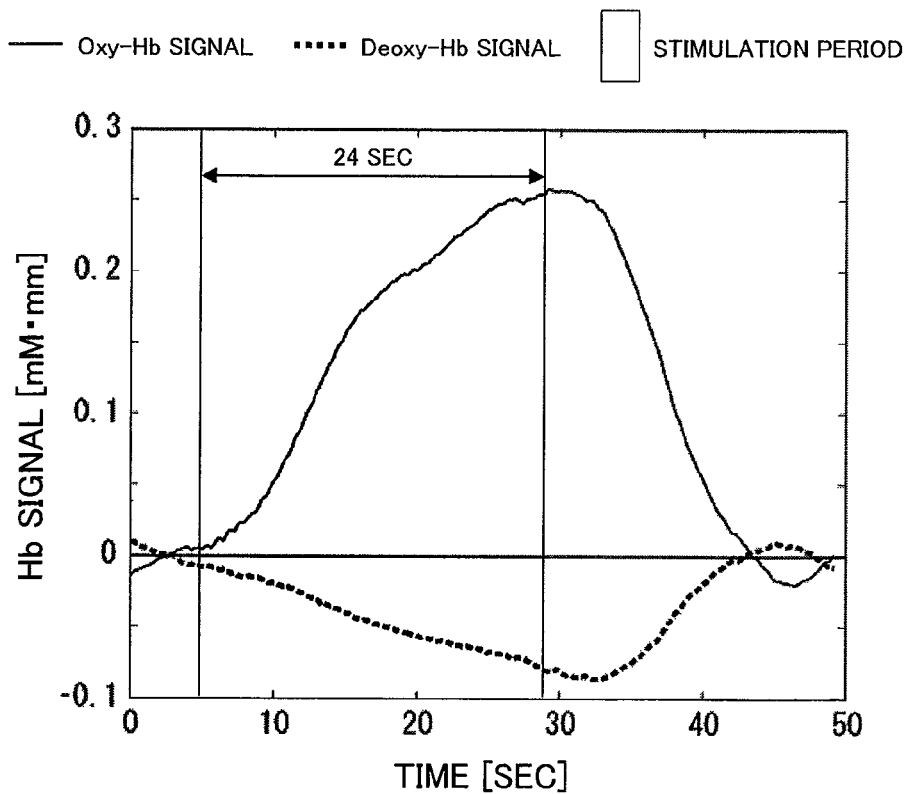
Figure 12:
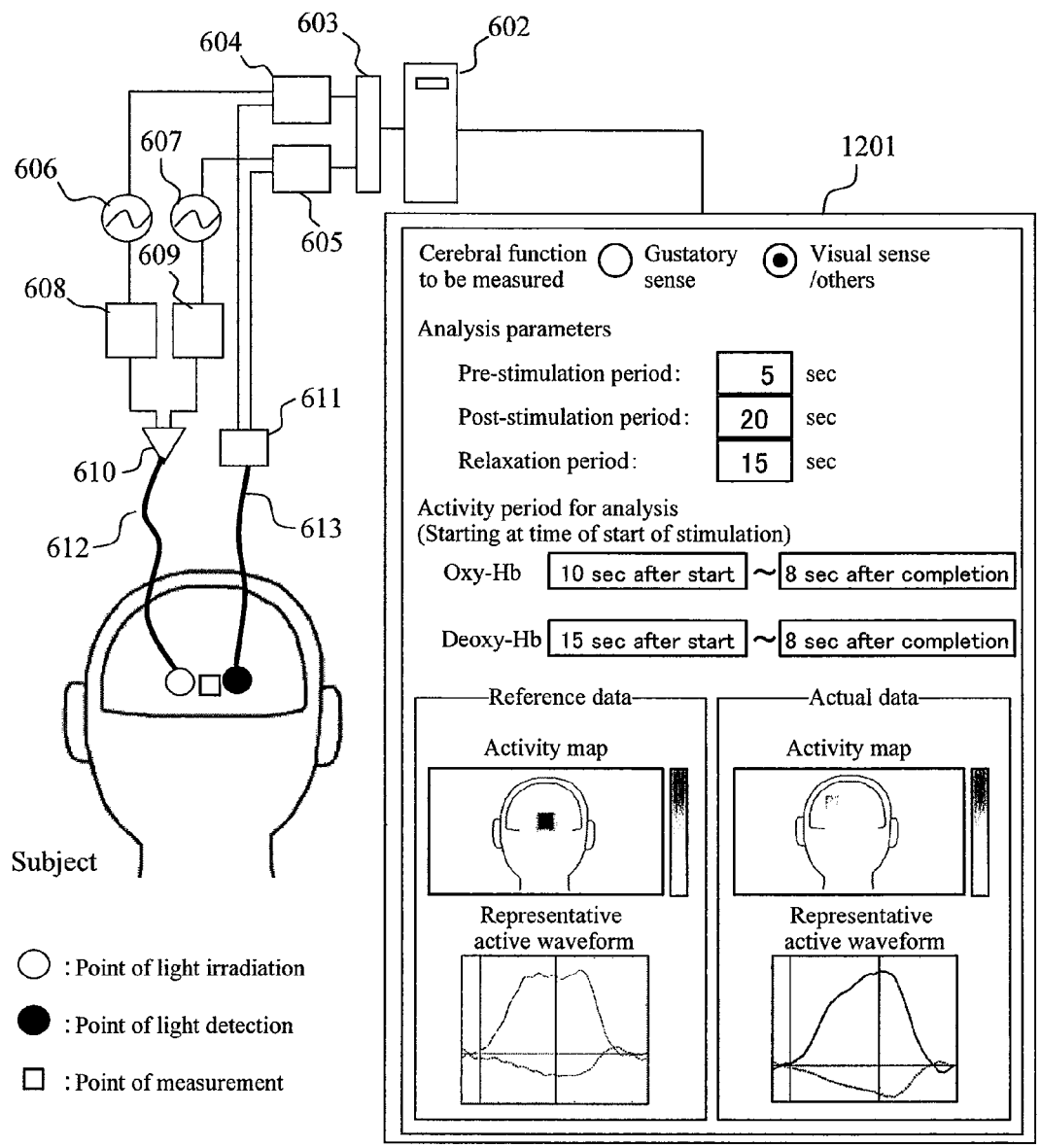
FIG. 12 is a block diagram showing the configuration of an instrument according to one embodiment of the present invention.
Figure 13:
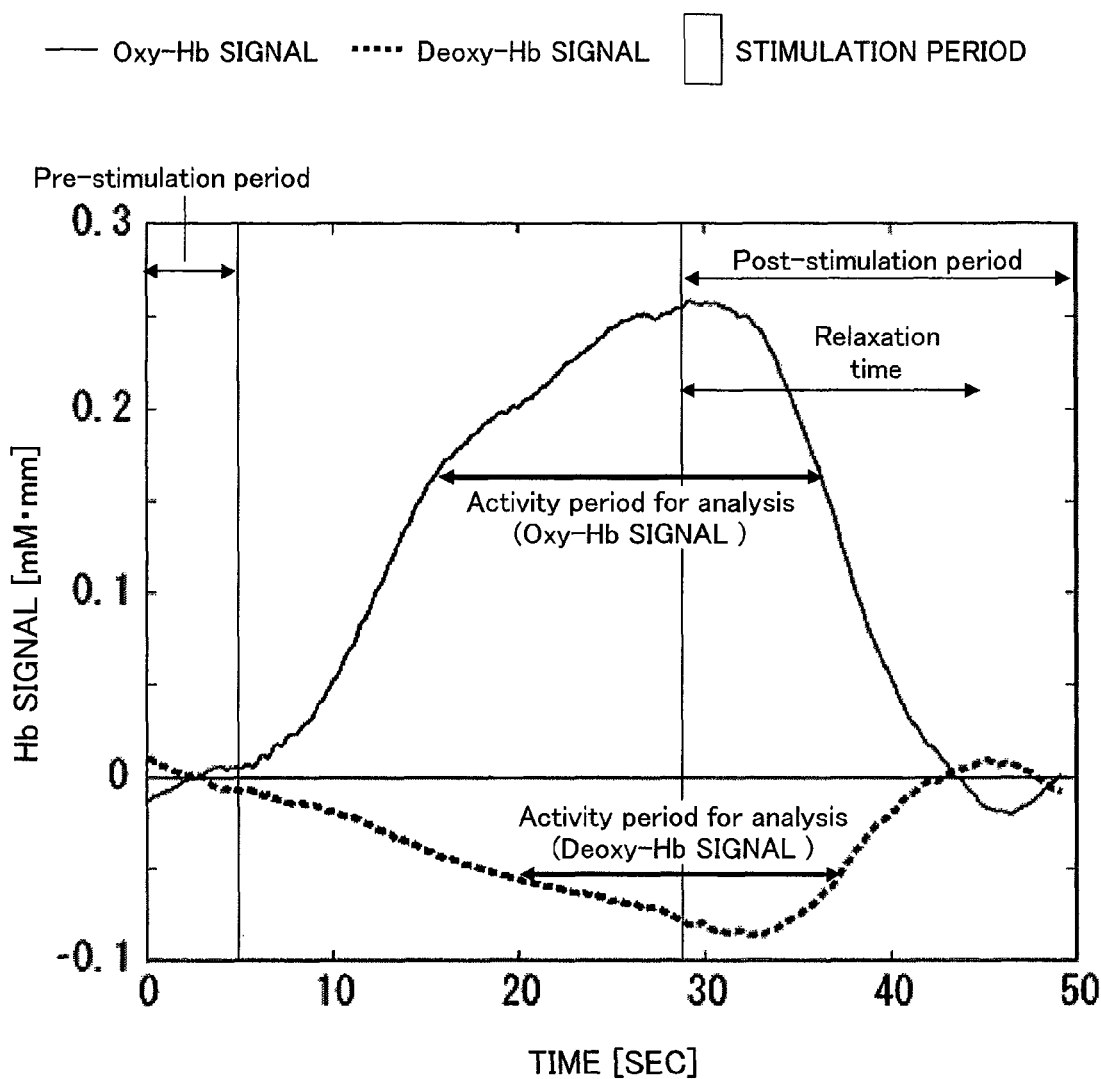
FIG. 13 is a graph showing an example of the Hb signals in the visual area.

FIGS. 12 and 13 show an example of data analysis in an instance where the "visual sense/others" is selected as the function to be measured, in comparison with the analysis method for the gustatory area measurement. The main points of difference between these measurements are the pre-stimulation period, the relaxation period, and the activity period for analysis, which results from a difference in the waveform of the activity signal. As shown in FIGS. 1 and 4, the activity of the visual area is as follows: the oxy-Hb signal starts increasing immediately after the start of stimulation and reaches the vicinity of its maximum value in about 10 seconds, and after the completion of the stimulation, the oxy-Hb signal starts decreasing after a lapse of 0 to 5 seconds and returns to its original base line within 15 seconds after the completion of the stimulation. As for the deoxy-Hb signal that decreases as opposed to the oxy-Hb signal, the deoxy-Hb signal exhibits a basically similar pattern of change with time to the oxy-Hb signal although having the characteristic of taking slightly more time to start decreasing, and thus, the deoxy-Hb signal returns to its original base line within 15 seconds after the completion of the stimulation. Thus, the post-stimulation period and the relaxation period can be set to 20 seconds or more and 15 seconds or more, respectively, which are sufficient for ordinary cases. As for the activity period for analysis, the activity period for analysis is set based on the typical active waveforms from the visual area shown in FIG. 1. Specifically, as shown for example in FIG. 12, the period between the instant after a lapse of 10 seconds, after the start of the stimulation and the instant after a lapse of 8 seconds, after the completion of the stimulation is set as the activity period for analysis for the oxy-Hb signal, while the period between the instant after a lapse of 15 seconds, after the start of the stimulation and the instant after a lapse of 8 seconds, after the completion of the stimulation is set as the activity period for analysis for the deoxy-Hb signal.

The "presentation function for measurement method" and the "data analysis function" described above are characterized by having and using a database on "measurement parameters" and "analysis parameters" according to cerebral function to be measured. The database is stored in the memory of the control unit 602. FIG. 14 shows an example of storage of various parameters. The database is designed to provide parameters suitable for stimulation when a measurer sets the cerebral function to be measured and specific stimulation therefor.

Incidentally, the data on the gustatory sense, stored in the database as the measurement parameters and analysis parameters for cerebral function measurement, may be applied, as they are, to gustatory function measurement based on the physiological change caused by the salivary gland.

Second Embodiment

Figure 15:
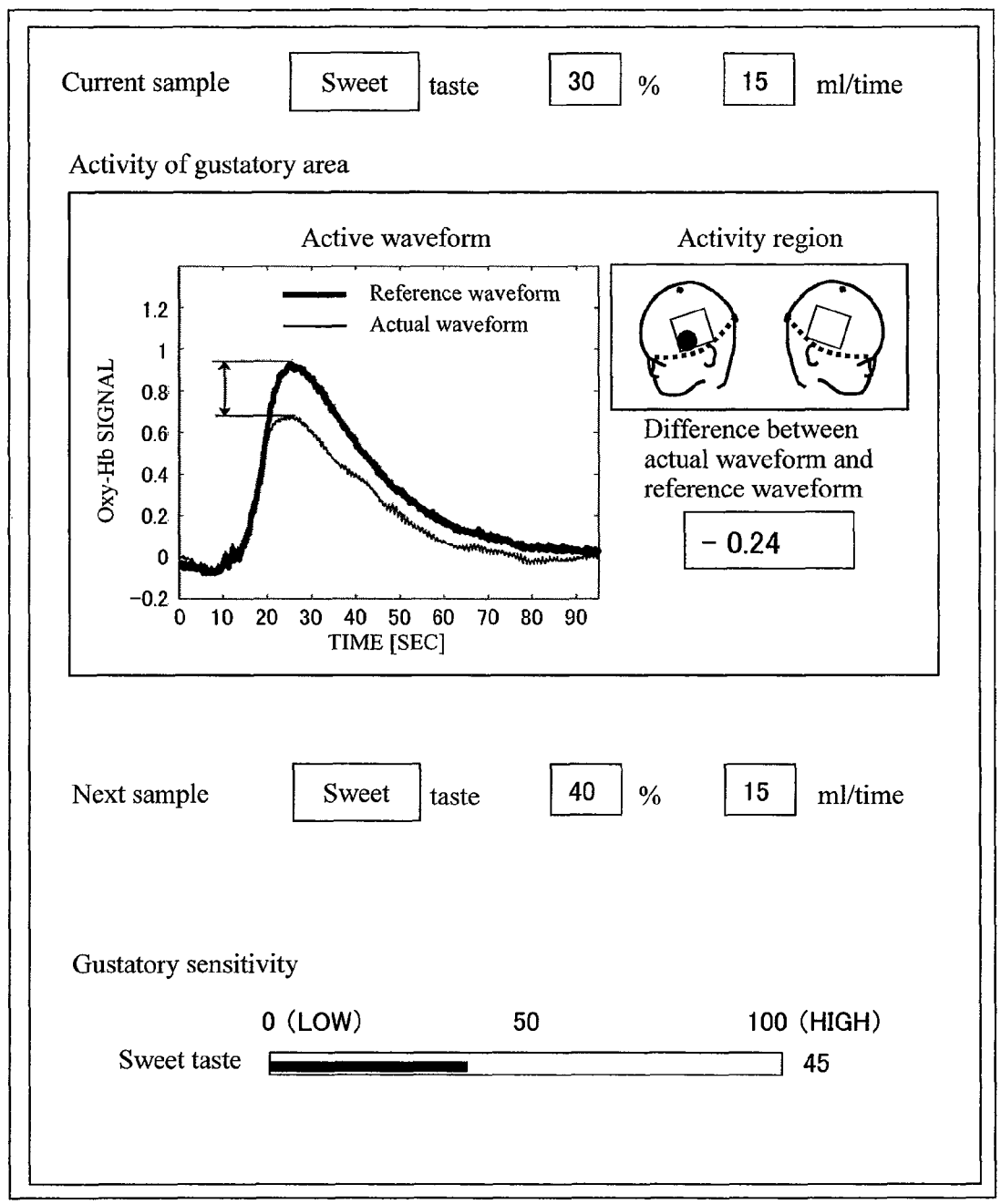
FIG. 15 is an illustration showing an example of a display screen of a gustatory sense measurement instrument.
Figure 17:
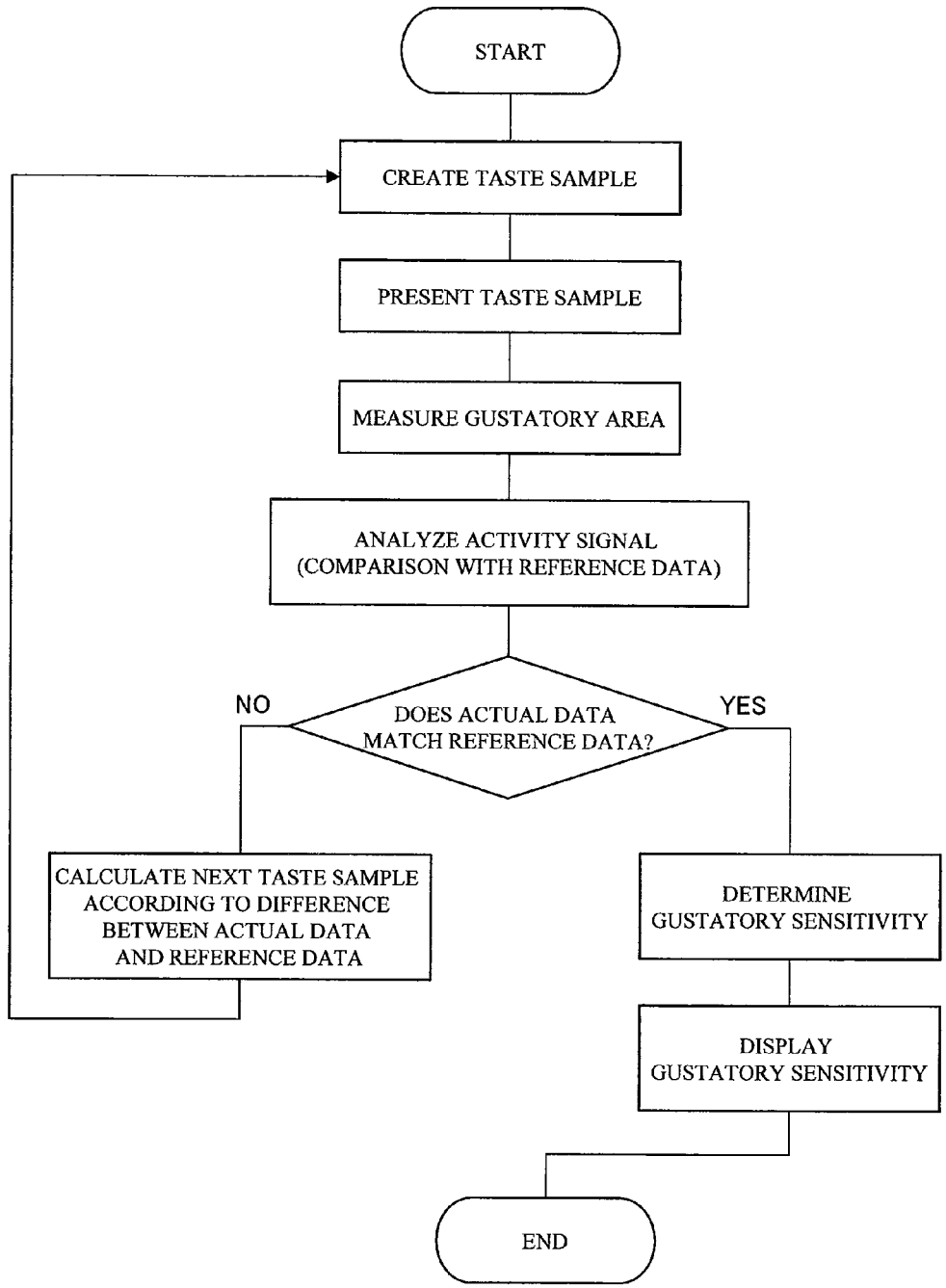
FIG. 17 is a flowchart showing an example of a method for gustatory sensitivity evaluation process, which is executed by the gustatory sense measurement instrument.

The second embodiment provides a gustatory sense measurement instrument using the biological optical measurement instrument according to the first embodiment. FIG. 15 shows an example of a screen on which gustatory sensitivity to "sweetness" is being measured. Display items include the properties of a currently presented sample (e.g., the taste, the concentration, the dose, etc.), the measured activity of the gustatory area (e.g., the active waveforms of the Hb signals, the activity part, etc.), comparison with reference data for evaluation of the gustatory sensitivity, the properties of a sample to be next presented (e.g., the taste, the concentration, the dose, etc.), and a graph showing the gustatory sensitivity of the subject. As shown for example in FIG. 15, the evaluation of the gustatory sensitivity is done according to the difference between the activity of the gustatory area for the current sample and the reference data, in order to accurately measure the gustatory sensitivity. For example, a difference in peak value between measured data and the reference data, or a relative value based on a correlation coefficient with the reference data can be used to evaluate the gustatory sensitivity. As shown in a flowchart of FIG. 17, a method may be adopted which involves determining the sample to be next presented according to the difference between the current activity of the gustatory area (or the Hb signals) and the reference data, and repeating this operation until the measured activity of the gustatory area approaches the reference data, thereby accurately evaluating the gustatory sensitivity. Although the oxy-Hb signal alone is shown in FIG. 15 as the activity of the gustatory area, the deoxy-Hb signal or a total-Hb signal indicative of the sum total of the oxy-Hb signal and the deoxy-Hb signal may be used.

Figure 16:
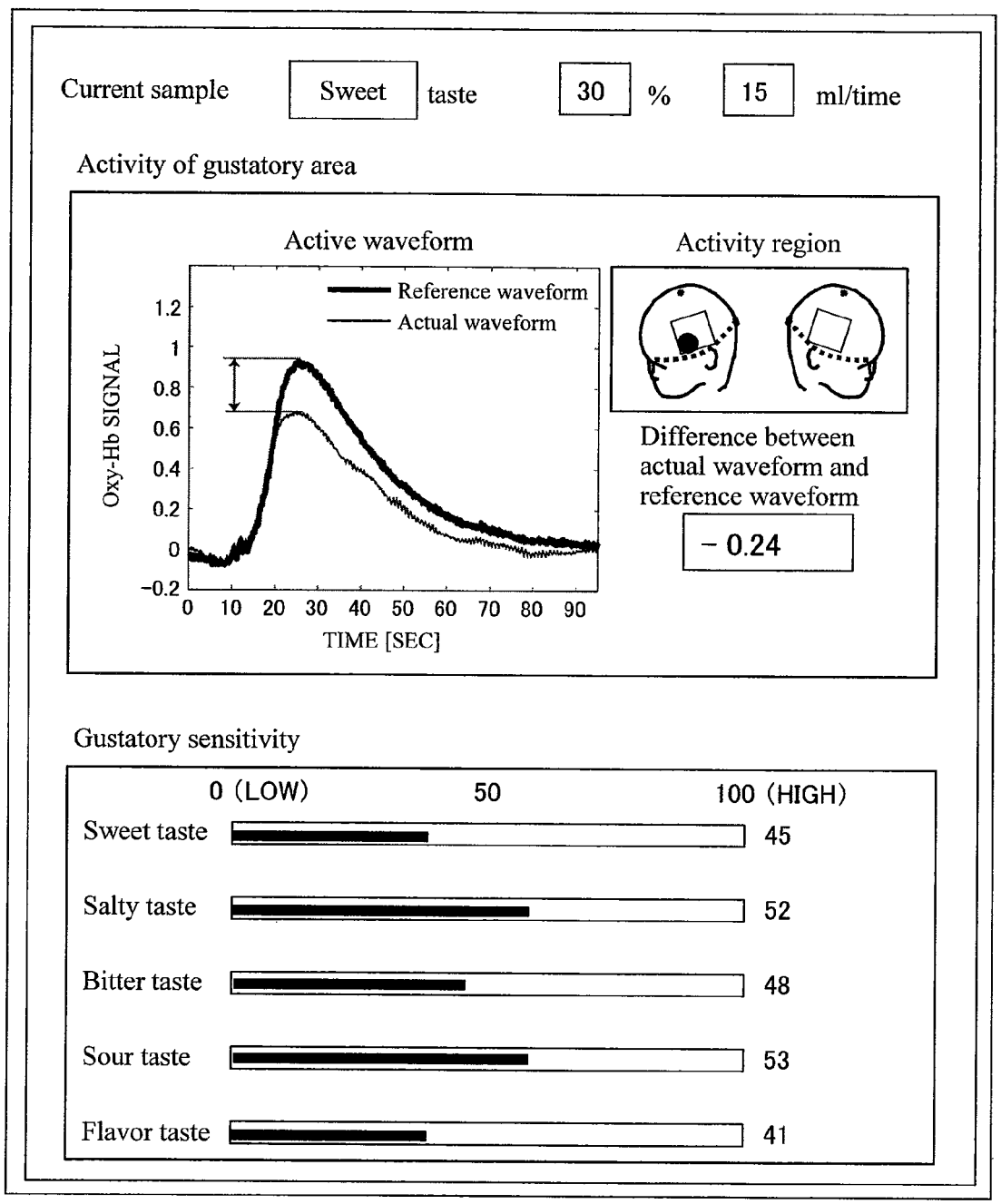
FIG. 16 is an illustration showing an example of the display screen of the gustatory sense measurement instrument.
Figure 18:
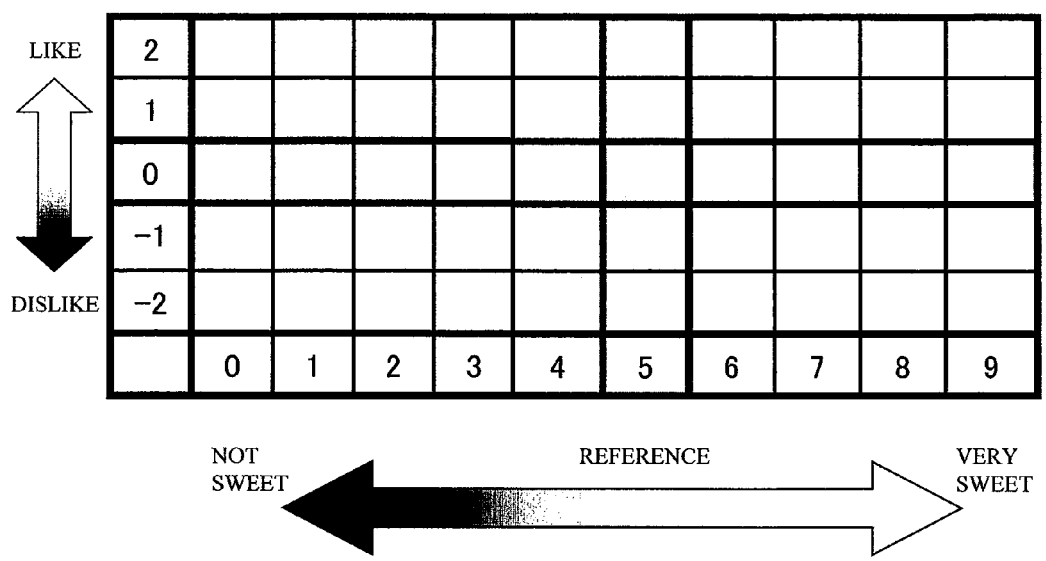
FIG. 18 is an illustration showing an example of a two-dimensional subjective evaluation table on the gustatory sense.
Figure 19:
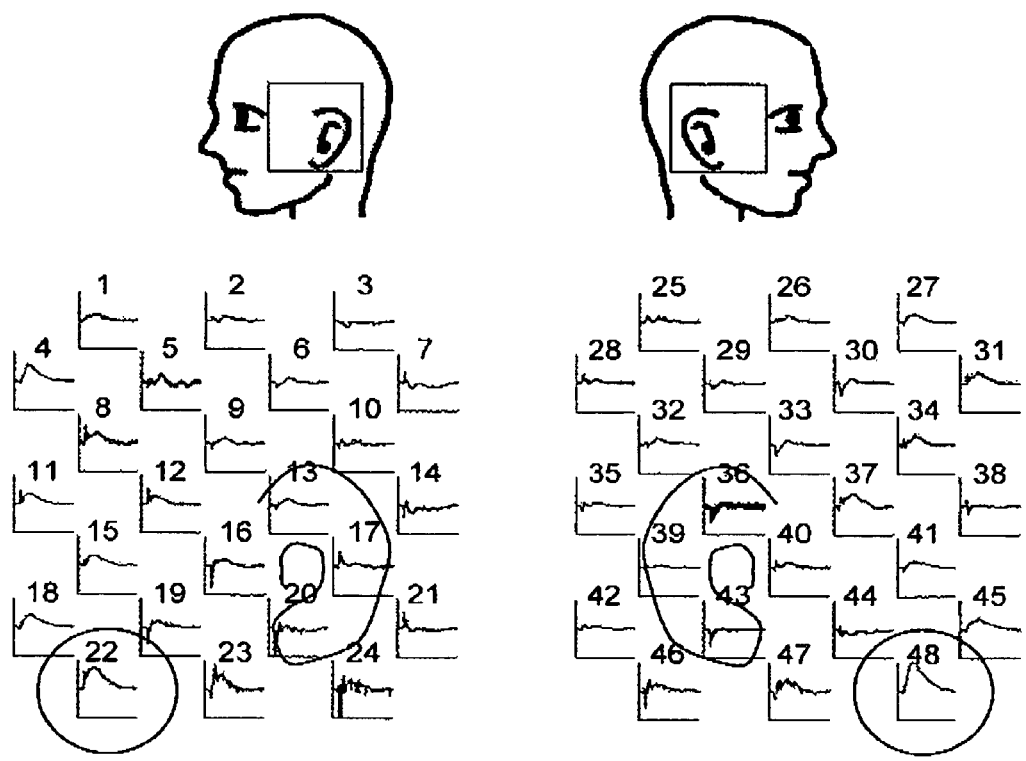
FIG. 19 is graphs showing physiological change data that reflects salivary gland function.

This gustatory sensitivity measurement can be carried out for five basic tastes consisting of a "sweet taste," a "salty taste," a "sour taste," a "bitter taste," and "flavor." These gustatory sensitivity measurements can be executed in sequence to finally evaluate the overall gustatory sensitivity as shown in FIG. 16. As shown in FIGS. 15 and 16, the activity of the frontal lobe (or the Hb signals) connected with subjective evaluation and taste evaluation by the subject, as well as the gustatory sense and the activity of the gustatory area (or the Hb signals), can be simultaneously measured to evaluate the gustatory sensitivity with higher accuracy. For example, a two-dimensional subjective evaluation table as shown in FIG. 18 is prepared in front of the subject, and after drinking a presented taste sample, the subject puts a drinking cup on an applicable square. This makes it possible to evaluate how the subject feels the taste on two axes: the "sweetness" axis and the "like-dislike" axis. The result of subjective evaluation and the result of cerebral activity measurement can be used in combination to evaluate not only the gustatory sensitivity but also a subject's subjective favorite taste. Moreover, electronic equipment having a pressure sensor may be used in place of the subjective evaluation table shown in FIG. 18 to automatically input the result of evaluation to an analyzer and also to measure weight and automatically measure and record the quantity of sample drunk by the subject.

Although description is herein given with regard to the gustatory sense measurement instrument using the biological optical measurement instrument that measures the gustatory area, the biological optical measurement instrument that measures the gustatory function based on the physiological change caused by the salivary gland may be used to construct the equal gustatory sense measurement instrument.

The gustatory sense measurement instrument according to the second embodiment can assist in diagnosis or rehabilitation of a gustatory disorder. The gustatory disorder is a disease observed about 14 in every 10000 people, and the diagnosis has to relay on patient's subjective information. Therefore, the gustatory sense measurement instrument has a high degree of effectiveness. Moreover, a person who has an occupation requiring an improvement in the gustatory sensitivity (e.g., a drink panelist, a taster, etc.) can use the instrument as part of gustatory sense training or gustatory sense testing.

When information on the subject's favorite taste is used, the instrument can be used as an assist tool for development of drinks or foods. Further, the instrument is useful for development of drinks and foods for babies and infants or pets that cannot give information on their favorite tastes.

What is claimed is:

1. A biological optical measurement instrument, comprising:
    a light irradiation means for irradiating the head of a subject with light;
    a light detection means for detecting transmitted light that is emitted from the light irradiation means, and that passes through a point of measurement in the head of the subject;
    an input unit where the type of cerebral function to be measured is inputted;
    a calculator that sets different analysis parameters according to the type of cerebral function inputted through the input unit, and that calculates an oxyhemoglobin concentration change signal and a deoxyhemoglobin concentration change signal at the point of measurement, on the basis of a signal detected by the light detection means, and on the basis of the analysis parameters; and
    a display unit that displays the result of calculation by the calculator,
    wherein the analysis parameters include a time parameter based on which a time period of absence of cerebral activity to be measured is set, and
    wherein, when the cerebral function to be measured is gustatory function, the time period of absence of cerebral activity to be measured is set based on time elapsed after a start of stimulation.

2. The biological optical measurement instrument according to claim 1, wherein,
    the time period of absence of cerebral activity to be measured is set so as not to contain a period of 60 seconds after start of stimulation, and.

3. The biological optical measurement instrument according to claim 1, wherein the analysis parameters include an activity period for analysis, which is a period for evaluation of the presence or absence of the cerebral activity, and if any, the intensity thereof.

4. The biological optical measurement instrument according to claim 3, wherein, the activity period for analysis for the oxyhemoglobin concentration change signal is set so as to contain a period between an instant after a lapse of 16 seconds, and an instant after a lapse of 25 seconds, after start of stimulation, while the activity period for analysis for the deoxyhemoglobin concentration change signal is set so as to contain a period between an instant after a lapse of 28 seconds, and an instant after a lapse of 37 seconds after the start of the stimulation.

5. The biological optical measurement instrument according to claim 3, wherein any one of an average value and a maximum value of any of the oxyhemoglobin concentration change signal and the deoxyhemoglobin concentration change signal measured during the activity period for analysis is used to evaluate the presence or absence of the cerebral activity, and if any, the intensity thereof.

6. The biological optical measurement instrument according to claim 1, wherein the analysis parameters include reference waveform data on the cerebral activity, for evaluation of the presence or absence of the cerebral activity, and if any, the intensity thereof.

7. The biological optical measurement instrument according to claim 6, wherein, the reference waveform data on the activity for the oxyhemoglobin concentration change signal is a polynomial function having a maximum value in the period between the instant after a lapse of 16 seconds, and the instant after a lapse of 25 seconds, after start of stimulation, while the reference waveform data on the activity for the deoxyhemoglobin concentration change signal is a polynomial function having a minimum value in the period between the instant after a lapse of 28 seconds, and the instant after a lapse of 37 seconds, after the start of the stimulation.

8. The biological optical measurement instrument according to claim 6, wherein the analysis parameters are prestored in a storage unit.

9. A biological optical measurement instrument, comprising:
    a light irradiation means for irradiating a subject with light;

a light detection means for detecting transmitted light that is emitted from the light irradiation means, and that passes through a point of measurement in the subject;

an input unit where the type of physiological change to be measured is inputted;

a calculator that sets different analysis parameters according to the type of physiological change inputted through the input unit, and that calculates an oxyhemoglobin concentration change signal and a deoxyhemoglobin concentration change signal at the point of measurement, on the basis of a signal detected by the light detection means, and on the basis of the analysis parameters; and a display unit that displays the result of calculation by the calculator, wherein the analysis parameters include a time parameter based on which a time period of absence of physiological change to be measured is set, and wherein when the physiological change to be measured is salivary gland function, the time period of absence of physiological change to be measured is set based on time elapsed after a start of stimulation.

10. The biological optical measurement instrument according to claim 9, wherein, the time period of absence of physiological change to be measured is set so as not to contain a period of 60 seconds after start of stimulation.

11. The biological optical measurement instrument according to claim 9, wherein the analysis parameters include an activity period for analysis, which is a period for evaluation of the presence or absence of the physiological change, and if any, the intensity thereof.

12. The biological optical measurement instrument according to claim 11, wherein, the activity period for analysis for the oxyhemoglobin concentration change signal is set so as to contain a period between an instant after a lapse of 16 seconds, and an instant after a lapse of 25 seconds, after start of stimulation, while the activity period for analysis for the deoxyhemoglobin concentration change signal is set so as to contain a period between an instant after a lapse of 28 seconds, and an instant after a lapse of 37 seconds, after the start of the stimulation.

13. The biological optical measurement instrument according to claim 11, wherein any one of an average value and a maximum value of any of the oxyhemoglobin concentration change signal and the deoxyhemoglobin concentration change signal measured during the activity period for analysis is used to evaluate the presence or absence of the physiological change, and if any, the intensity thereof.

14. The biological optical measurement instrument according to claim 9, wherein the analysis parameters include reference waveform data on the physiological change, for evaluation of the presence or absence of the physiological change, and if any, the intensity thereof.

15. The biological optical measurement instrument according to claim 14, wherein, the reference waveform data on the activity for the oxyhemoglobin concentration change signal is a polynomial function having a maximum value in the period between the instant after a lapse of 16 seconds, and the instant after a lapse of 25 seconds, after start of stimulation, while the reference waveform data on the activity for the deoxyhemoglobin concentration change signal is a polynomial function having a minimum value in the period between the instant after a lapse of 28 seconds, and the instant after a lapse of 37 seconds, after the start of the stimulation.

16. The biological optical measurement instrument according to claim 14, wherein the analysis parameters are prestored in a storage unit.

* * * * *